United States Patent
Flohr et al.

(10) Patent No.: US 10,399,985 B2
(45) Date of Patent: Sep. 3, 2019

(54) (HETERO)ARYL IMIDAZOLES/PYRAZOLES FOR TREATMENT OF NEUROLOGICAL DISORDERS

(71) Applicant: Hoffmann-La Roche Inc., Little Falls, NJ (US)

(72) Inventors: Alexander Flohr, Loerrach (DE); Katrin Groebke Zbinden, Liestal (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 19 days.

(21) Appl. No.: 15/220,617

(22) Filed: Jul. 27, 2016

(65) Prior Publication Data

US 2016/0333018 A1 Nov. 17, 2016

Related U.S. Application Data

(60) Provisional application No. PCT/EP2015/051638, filed on Jan. 28, 2015.

(30) Foreign Application Priority Data

Jan. 31, 2014 (EP) .................................... 14153372

(51) Int. Cl.
*C07D 211/20* (2006.01)
*C07D 487/04* (2006.01)

(52) U.S. Cl.
CPC ................................. *C07D 487/04* (2013.01)

(58) Field of Classification Search
None
See application file for complete search history.

(56) References Cited

U.S. PATENT DOCUMENTS

2008/0090834 A1* 4/2008 Hoover ............... C07D 401/10
514/253.06

FOREIGN PATENT DOCUMENTS

| WO | 2013/000994 A1 | 1/2013 |
| WO | 2013/052526 A1 | 4/2013 |
| WO | 2014/072261 A1 | 5/2014 |

OTHER PUBLICATIONS

Nakazato et al., "Recent advances in novel atypical antipsychotic agents: potential therapeutic agents for the treatment of schizophrenia" Expert Opinion on Therapeutic Patents 10(1):75-98 ( 2000)

* cited by examiner

*Primary Examiner* — Layla Soroush
(74) *Attorney, Agent, or Firm* — Brian L. Buckwalter

(57) ABSTRACT

The present invention relates to compounds of formula I, wherein A, B, $R^1$, $R^2$, and Z are as defined hereinbefore.

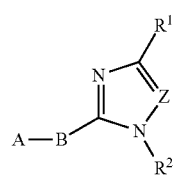

(I)

11 Claims, No Drawings

(HETERO)ARYL IMIDAZOLES/PYRAZOLES FOR TREATMENT OF NEUROLOGICAL DISORDERS

CROSS REFERENCE TO RELATED APPLICATIONS

This application is a continuation of International Application No. PCT/EP2015/051638 having an international filing date of Jan. 28, 2015 and which claims benefit under 35 U.S.C. § 119 to European Patent Application No. 14153372.9 filed Jan. 31, 2014. The entire contents of both are incorporated herein by reference.

FIELD OF THE INVENTION

The present invention relates to novel compounds of formula I, wherein wherein A, B, X, Y, Z, $R^1$, $R^2$, $R^3$, $R^4$, $R^5$ and $R^6$ are as defined are as described herein, having pharmaceutical activity, their manufacture, pharmaceutical compositions containing them and their potential use as medicaments.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach, besides ameliorating positive symptoms in schizophrenic patients, poorly addresses negative and cognitive symptoms which are the best predictors of functional outcome (Sharma T., Br. J. Psychiatry, 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

There is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-1127, Soderling S. H., et al., Proc Natl Acad Sci USA (1999) 96(12):7071-7076, Loughney K., et al., Gene (1999) 234 (1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididymal sperm (Coskran T. M, et al., J. Histochem. Cytochem. 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition. Inhibition of this enzyme pharmacologically or through gene disruption causes a reduction in activity and a reduced response to psychomotor stimulants. Inhibition also reduces the conditioned avoidance response, a behavioral response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., Eur. J. Neuroscience 2005, 2: 1070-1076), In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

BRIEF SUMMARY OF THE INVENTION

The present invention relates to compounds having formula (I)

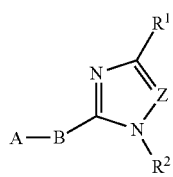

wherein A is

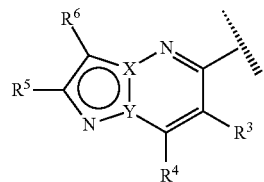

$R^1$ is selected from aryl or heteroaryl,
$R^2$ is selected from hydrogen or $C_{1-7}$ alkyl,
$R^3$ is selected from hydrogen or $C_{1-7}$ alkyl,
$R^4$ is selected from hydrogen, $C_{1-7}$ alkyl, $C_{1-7}$ alkoxy or C(O)NR'R", $R^5$ is selected from $C_{1-7}$ alkyl, $C_{3-8}$ cycloalkyl, $C_{1-7}$ haloalkyl, cyano, C(O)NR'R", $R^6$ is selected from hydrogen, $C_{1-7}$ alkyl or $C_{1-7}$ hydroxyalkyl, or
$R^5$ and $R^6$ form together $C_{3-8}$ cycloalkyl,
R' and R" are in each occurrence independently selected from hydrogen and $C_{1-7}$ alkyl,
X and Y are independently selected from C or N, with the proviso that X and Y are not simultaneously N,
Z is selected from CH or N,
B is selected from $C_1$-$C_4$-alkylene, $C_2$-$C_4$-alkenylene, $C_2$-$C_4$-alkynylene, —O—$C_1$-$C_4$-alkyl.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

Unless otherwise indicated, the following definitions are set forth to illustrate and define the meaning and scope of the various terms used to describe the invention herein.

The terms "compound(s) of the formula (I), "compound(s) of formula (I)", "compound(s) of this invention" or "compound(s) of the present invention" refer to any compound selected from the genus of compounds as defined by the formula (I) including stereoisomers, tautomers, solvates, and salts (e.g. pharmaceutically acceptable salts) thereof.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "halogen" refers to fluorine, chlorine, bromine and iodine, more superficially fluorine, chlorine and bromine.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "alkenylene" denotes a linear divalent hydrocarbon chain of 2 to 7 carbon atoms or a branched divalent hydrocarbon chain of 3 to 7 carbon atoms with at least one double bond. Exemplary alkenylene include ethenylene, 2,2-dimethylethenylene, propenylene, 2-methylpropenylene, butenylene, and pentenylene.

The term "alkynylene" denotes a linear divalent hydrocarbon chain of 2-6 carbon atoms or a branched hydrocarbon chain of 3-6 carbon atoms with at least one triple bond. Exemplary alkynylene include ethynylene, 2,2-dimethylethynylene, propynylene, 2-methylpropynylene, butynylene, and pentynylene.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "alkoxy" denotes a group of the formula —O—R', wherein R' is an alkyl group. Examples of alkoxy moieties include methoxy, ethoxy, isopropoxy, and tert-butoxy.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "aryl" denotes a monovalent aromatic carbocyclic mono- or bicyclic ring system comprising 6 to 10 carbon ring atoms. Examples of aryl moieties include phenyl and naphthyl The term "amino" refers to a monovalent group that has a nitrogen atom with two hydrogen atoms (represented by —$NH_2$).

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "oxo" when referring to substituents on heterocycloalkyl means that an oxygen atom is attached to the heterocycloalkyl ring. Thereby, the "oxo" may either replace two hydrogen atoms on a carbon atom, or it may simply be attached to sulfur, so that the sulfur exists in oxidized form, i.e. bearing one or two oxygens.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "azaspirocycloalkyl" refers to a monovalent saturated 7- to 11-membered bicyclic moiety with the rings connected through one atom, containing one, two or three N heteroatoms, the remaining ring atoms being carbon atoms, wherein the point of attachment can be through either a carbon atom or a heteroatom.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

Structures depicted herein are also meant to include compounds that differ only in the presence of one or more isotopically enriched atoms. For example wherein one or more hydrogen atoms are replaced by deuterium, or one or more carbon atoms are replaced by a $^{13}$C- or $^{14}$C-enriched carbon are within the scope of this invention.

The definitions described herein apply irrespective of whether the terms in question appear alone or in combination. It is contemplated that the definitions described herein may be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

Compounds of formula I can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

The present invention relates to compounds having formula (I)

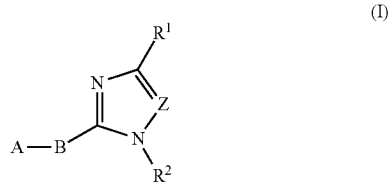

(I)

wherein A is

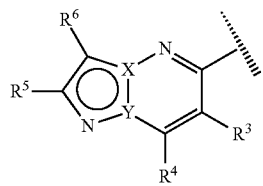

$R^1$ is selected from aryl or heteroaryl,
$R^2$ is selected from hydrogen or $C_{1-7}$ alkyl,
$R^3$ is selected from hydrogen or $C_{1-7}$ alkyl,
$R^4$ is selected from hydrogen, $C_{1-7}$ alkyl, $C_{1-7}$ alkoxy, C(O)NR'R'',
$R^5$ is selected from $C_{1-7}$ alkyl, $C_{3-8}$ cycloalkyl, $C_{1-7}$ haloalkyl, cyano, C(O)NR'R'', $R^6$ is selected from hydrogen, $C_{1-7}$ alkyl, $C_{1-7}$ hydroxyalkyl, or
$R^5$ and $R^6$ form together $C_{3-8}$ cycloalkyl,
R' and R'' in each occurrence are independently selected from hydrogen and $C_{1-7}$ alkyl, X and Y are independently selected from C or N, with the proviso that X and Y are not simultaneously N,
Z is selected from CH or N,
B is selected from $C_1$-$C_4$-alkylene, $C_2$-$C_4$-alkenylene, $C_2$-$C_4$-alkynylene, —O—$C_1$-$C_4$-alkyl.

In a particular embodiment the present invention relates to compounds of formula (I), wherein $R^1$ is selected from aryl or heteroaryl,
$R^2$ is selected from hydrogen, $C_{1-7}$ alkyl,
$R^3$ is selected from hydrogen, $C_{1-7}$ alkyl,
$R^4$ is selected from hydrogen, $C_{1-7}$ alkyl, C(O)NR'R'', R' and R'' are independently selected from hydrogen and $C_{1-7}$ alkyl,
$R^5$ is selected from $C_{1-7}$ alkyl, $C_{3-8}$ cyclopropyl, $C_{1-7}$ haloalkyl, cyano,
$R^6$ is selected from hydrogen, $C_{1-7}$ alkyl, $C_{1-7}$ hydroxyalkyl,
X and Y are independently selected from C or N, with the proviso that X and Y are not simultaneously N,
Z is selected from CH or N,
B is selected from $C_1$-$C_4$-alkylene, $C_2$-$C_4$-alkenylene, $C_2$-$C_4$-alkynylene, In a particular embodiment the present invention relates to compounds of formula (I), wherein Z is CH.

In a particular embodiment the present invention relates to compounds of formula (I), wherein $R^1$ is selected from a six membered aryl or a six membered heteroaryl group comprising at least one N atom.

In a particular embodiment the present invention relates to compounds of formula (I), wherein $R^1$ is selected from phenyl, pyridazinyl, pyrimidinyl, pyridinyl or pyrazinyl. In one subembodiment the present invention relates to compounds of formula (I) wherein $R^1$ is phenyl.

In a particular embodiment the present invention relates to compounds of formula (I) wherein Z is CH and $R^1$ is selected from phenyl, pyridazinyl, pyrimidinyl, pyridinyl or pyrazinyl. In one subembodiment the present invention relates to compounds of formula (I) wherein Z is CH and $R^1$ is phenyl.

In a particular embodiment the present invention relates to compounds of formula (I), wherein B is selected from ethylene, ethenylene, ethynylene or —OCH$_2$—.

In a particular embodiment the present invention relates to compounds of formula (I), wherein B is selected from ethylene, ethenylene, ethynylene. In a particular subembodiment B is selected from ethylene, ethenylene, ethynylene, Z is CH and $R^1$ is selected from phenyl, pyridazinyl, pyrimidinyl, pyridinyl or pyrazinyl. In a another subembodiment B is selected from ethylene, ethenylene, ethynylene, Z is CH and $R^1$ is phenyl. In a another subembodiment B is selected from ethylene, Z is CH and $R^1$ is phenyl. In a another subembodiment B is selected from ethenylene, Z is CH and $R^1$ is phenyl. In a another subembodiment B is selected from ethynylene, Z is CH and $R^1$ is phenyl.

In a particular embodiment the present invention relates to compounds of formula (I), wherein A is selected from the group consisting of:

a)

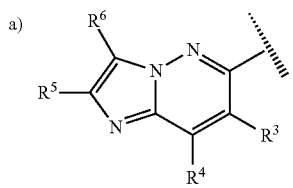

-continued b) 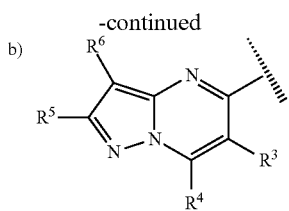

wherein R³ is hydrogen or methyl,
R⁴ is hydrogen, methyl, methoxy or C(O)NR'R" wherein R' and R" are independently selected from hydrogen and methyl,
R⁵ is methyl, ethyl, cyclopropyl, halomethyl, cyano or —C(O)NH₂,
R⁶ is hydrogen, methyl or hydroxymethyl.

In a particular embodiment the present invention relates to compounds of formula (I), wherein A is selected from the group consisting of:

a) 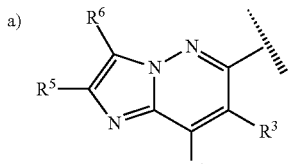

b) 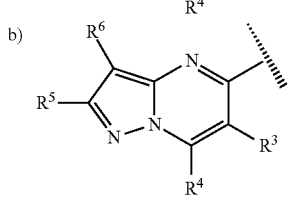

wherein R³ is hydrogen or methyl,
R⁴ is hydrogen, methyl or C(O)NR'R" wherein R' and R" are independently selected from hydrogen and methyl,
R⁵ is methyl, cyclopropyl, halomethyl or cyano,
R⁶ is methyl or hydroxymethyl.

In a particular embodiment the present invention relates to compounds of formula (I), wherein A is a) 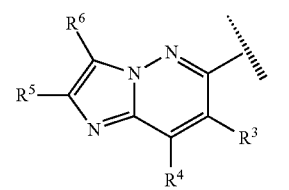

In a particular embodiment of the present invention the compounds of formula I are selected from the group consisting of:
2,3-dimethyl-6-((1-methyl-4-phenyl-1H-imidazol-2-yl)ethynyl)imidazo[1,2-b]pyridazine
2,3,7,8-tetramethyl-6-((1-methyl-4-phenyl-1H-imidazol-2-yl)ethynyl)imidazo[1,2-b]pyridazine
(2-methyl-6-((1-methyl-4-phenyl-1H-imidazol-2-yl)ethynyl)imidazo[1,2-b]pyridazin-3-yl)methanol
2,3-dimethyl-5-((1-methyl-4-phenyl-1H-imidazol-2-yl)ethynyl)pyrazolo[1,5-a]pyrimidine
3-methyl-6-((1-methyl-4-phenyl-1H-imidazol-2-yl)ethynyl)-2-(trifluoromethyl)imidazo[1,2-b]pyridazine
(2-cyclopropyl-6-((1-methyl-4-phenyl-1H-imidazol-2-yl)ethynyl)imidazo[1,2-b]pyridazin-3-yl)methanol
2-(difluoromethyl)-3-methyl-6-((1-methyl-4-phenyl-1H-imidazol-2-yl)ethynyl)imidazo[1,2-b]pyridazine
6-(1-Methyl-4-phenyl-1H-imidazol-2-ylethynyl)-2-trifluoromethyl-imidazo[1,2-b]pyridazine
3-Methyl-6-(1-methyl-4-phenyl-1H-imidazol-2-ylethynyl)-imidazo[1,2-b]pyridazine-2-carbonitrile
2-cyclopropyl-3-methyl-6-((1-methyl-4-phenyl-1H-imidazol-2-yl)ethynyl)imidazo[1,2-b]pyridazine
(E)-2,3-dimethyl-6-(2-(1-methyl-3-phenyl-1H-1,2,4-triazol-5-yl)vinyl)imidazo[1,2-b]pyridazine
(E)-3-methyl-6-(2-(1-methyl-4-phenyl-1H-imidazol-2-yl)vinyl)imidazo[1,2-b]pyridazine-2-carbonitrile
2,3-dimethyl-6-(2-(1-methyl-4-phenyl-1H-imidazol-2-yl)ethyl)imidazo[1,2-b]pyridazine
2,3,7,8-tetramethyl-6-(2-(1-methyl-4-phenyl-1H-imidazol-2-yl)ethyl)imidazo[1,2-b]pyridazine
(2-methyl-6-(2-(1-methyl-4-phenyl-1H-imidazol-2-yl)ethyl)imidazo[1,2-b]pyridazin-3-yl)methanol
2,3-dimethyl-5-(2-(1-methyl-4-phenyl-1H-imidazol-2-yl)ethyl)pyrazolo[1,5-a]pyrimidine
3-methyl-6-(2-(1-methyl-4-phenyl-1H-imidazol-2-yl)ethyl)-2-(trifluoromethyl)imidazo[1,2-b]pyridazine
(2-cyclopropyl-6-(2-(1-methyl-4-phenyl-1H-imidazol-2-yl)ethyl)imidazo[1,2-b]pyridazin-3-yl)methanol
2-(difluoromethyl)-3-methyl-6-(2-(1-methyl-4-phenyl-1H-imidazol-2-yl)ethyl)imidazo[1,2-b]pyridazine
6-(2-(1-methyl-4-phenyl-1H-imidazol-2-yl)ethyl)-2-(trifluoromethyl)imidazo[1,2-b]pyridazine
2,3-dimethyl-6-(2-(1-methyl-3-phenyl-1H-1,2,4-triazol-5-yl)ethyl)imidazo[1,2-b]pyridazine
3-Methyl-6-[2-(1-methyl-4-phenyl-1#H!-imidazol-2-yl)-ethyl]-imidazo[1,2-b]pyridazine-2-carbonitrile
2,3-dimethyl-6-(2-(1-methyl-4-(pyrimidin-2-yl)-1H-imidazol-2-yl)ethyl)imidazo[1,2-b]pyridazine
2,3-dimethyl-6-(2-(1-methyl-4-(pyridin-3-yl)-1H-imidazol-2-yl)ethyl)imidazo[1,2-b]pyridazine
2,3-dimethyl-6-(2-(1-methyl-4-(pyridin-4-yl)-1H-imidazol-2-yl)ethyl)imidazo[1,2-b]pyridazine
2,3-dimethyl-6-(2-(1-methyl-4-(pyrimidin-5-yl)-1H-imidazol-2-yl)ethyl)imidazo[1,2-b]pyridazine
2,3-dimethyl-6-(2-(1-methyl-4-(pyridin-2-yl)-1H-imidazol-2-yl)ethyl)imidazo[1,2-b]pyridazine
2,3-dimethyl-6-(2-(1-methyl-4-(pyridazin-4-yl)-1H-imidazol-2-yl)ethyl)imidazo[1,2-b]pyridazine
2,3-dimethyl-6-(2-(1-methyl-4-(pyrazin-2-yl)-1H-imidazol-2-yl)ethyl)imidazo[1,2-b]pyridazine
3,8-dimethyl-6-(2-(1-methyl-4-(pyridin-2-yl)-1H-imidazol-2-yl)ethyl)-2-(trifluoromethyl)imidazo[1,2-b]pyridazine
N,3-dimethyl-6-(2-(1-methyl-4-(pyridin-2-yl)-1H-imidazol-2-yl)ethyl)-2-(trifluoromethyl)imidazo[1,2-b]pyridazine-8-carboxamide
2,3-dimethyl-6-((1-methyl-3-phenyl-1H-1,2,4-triazol-5-yl)methoxy)imidazo[1,2-b]pyridazine
2,3,7,8-tetramethyl-6-((1-methyl-4-phenyl-1H-imidazol-2-yl)methoxy)imidazo[1,2-b]pyridazine
2-ethyl-3-methyl-6-((1-methyl-4-phenyl-1H-imidazol-2-yl)methoxy)imidazo[1,2-b]pyridazine
2-ethyl-3-methyl-6-((1-methyl-4-phenyl-1H-imidazol-2-yl)methoxy)imidazo[1,2-b]pyridazine
3-methyl-6-((1-methyl-4-phenyl-1H-imidazol-2-yl)methoxy)-2-(trifluoromethyl)imidazo[1,2-b]pyridazine
2-cyclopropyl-6-((1-methyl-4-phenyl-1H-imidazol-2-yl)methoxy)imidazo[1,2-b]pyridazine  2-methyl-6-((1-methyl-4-phenyl-1H-imidazol-2-yl)methoxy)imidazo[1,2-b]pyridazine 3-methyl-6-((1-methyl-4-phenyl-1H-imidazol-2-yl)
methoxy)imidazo[1,2-b]pyridazine-2-carboxamide 3-methyl-6-((1-methyl-4-phenyl-1H-imidazol-2-yl)
methoxy)imidazo[1,2-b]pyridazine-2-carbonitrile 8-methoxy-3-methyl-6-((1-methyl-4-phenyl-1H-imidazol-
2-yl)methoxy)-2-(trifluoromethyl)imidazo[1,2-b]
pyridazine (3-methyl-6-((1-methyl-4-phenyl-1H-imidazol-2-yl)
methoxy)imidazo[1,2-b]pyridazin-2-yl)methanol (2-cyclopropyl-6-((1-methyl-4-phenyl-1H-imidazol-2-yl)
methoxy)imidazo[1,2-b]pyridazin-3-yl)methanol 6-((1-methyl-4-phenyl-1H-imidazol-2-yl)methoxy)-2-(trif-
luoromethyl)imidazo[1,2-b]pyridazine 2,3-dimethyl-5-((1-methyl-4-phenyl-1H-imidazol-2-yl)
methoxy)pyrazolo[1,5-a]pyrimidine 2-[(1-Methyl-4-phenyl-imidazol-2-yl)methoxy]-7,8-di-
hydro-6H-cyclopenta[1,2]imidazo[3,4-c]pyridazine.

In another aspect the present invention relates to a process for the manufacture of a compound of formula I, wherein B is ethynylene, comprising:

a) reacting a compound of formula II

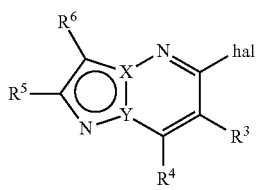

(II)

b) with a compound of formula III

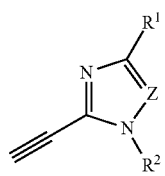

(III)

c) to yield a compound of formula I, wherein $R^1$, $R^2$, $R^3$, $R^4$, $R^5$, $R^6$ and Z are as defined hereinbefore.

In another aspect the present invention relates to a process for the manufacture of a compound of formula I, wherein B is ethylene or ethenylene, comprising:

a) reacting a compound of formula IIa

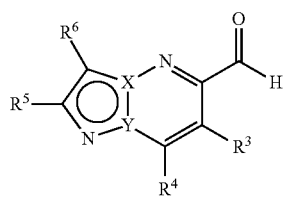

(IIa)

b) with a compound of formula IV

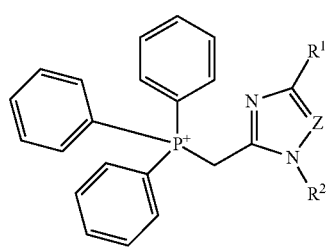

(IV)

to yield a compound of formula I and optionally hydrogenation or c) reacting a compound of formula V

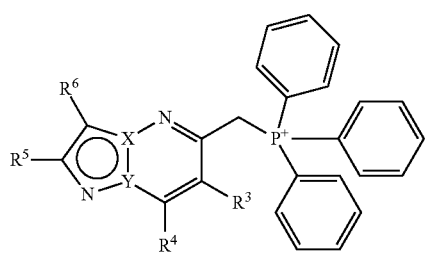

(V)

d) with a compound of formula IIa

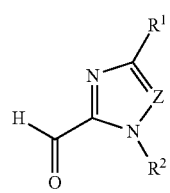

(IIIa)

to yield a compound of formula I and optionally hydrogenation, wherein $R^1$, $R^2$, $R^3$, $R^4$, $R^5$, $R^6$ and Z are as defined hereinbefore.

In another aspect the present invention relates to a process for the manufacture of a compound of formula I, wherein B is —OCH$_2$—, comprising:

a) reacting a compound of formula II

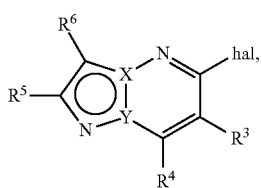

(II)

b) with a compound of formula IIb

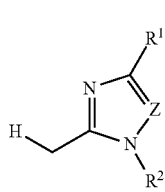

(IIIb)

to yield a compound of formula I, wherein R1, R2, R3, R4, R5, R6 and Z are as defined hereinbefore In a further aspect the present invention relates to the use of a compound of formula I for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In a further aspect the present invention relates to the use of a compound of formula I for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In a further aspect the present invention relates to a compound of formula I for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In a further aspect the present invention relates to a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound of formula I.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount may be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., ProcNatl Acad Sci USA (2000) 97(7): 3702-3707).

The human PDE10A full length assay was performed in 96-well micro titer plates. The reaction mixture of 50 µl contained 20 mM HEPES pH=7.5/10 mM MgCl2/0.05 mg/ml BSA (Sigma cat. # A-7906), 50 nM cGMP (Sigma, cat. # G6129) and 50 nM [3H]-cGMP (GE Healthcare, cat. # TRK392 S. A. 13.2 Ci/mmol), 3.75 ng/well PDE10A enzyme (Enzo Life Science, Lausen, Switzerland cat # SE-534) with or without a specific test compound. A range of concentrations of the potential inhibitor was used to generate data for calculating the concentration of inhibitor resulting in 50% of the effect (e.g. IC50, the concentration of the competitor inhibiting PDE10A activity by 50%). Non-specific activity was tested without the enzyme. The reaction was initiated by the addition of the substrate solution (cGMP and [3H]-cGMP) and allowed to progress for 20 minutes at room temperature. The reaction was terminated by adding 25 µl of YSi-SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) have an $IC_{50}$ value below 10 µM, more specifically below 5 µM, yet more specifically below 1 µM. The following table shows data for some examples.

| Example | $IC_{50}$ [µM] |
| --- | --- |
| 3 | 0.001 |
| 4 | 0.0015 |
| 6 | 0.0019 |
| 7 | 0.0466 |
| 8 | 0.001 |
| 10 | 0.012 |
| 11 | 0.0013 |
| 12 | 0.0138 |
| 14 | 0.0108 |
| 15 | 0.0034 |
| 16 | 0.0024 |
| 17 | 0.0205 |
| 18 | 0.6556 |
| 19 | 0.0064 |
| 20 | 0.0828 |
| 21 | 0.0277 |
| 22 | 0.0054 |
| 23 | 0.0092 |
| 24 | 1.688 |
| 25 | 0.0323 |
| 26 | 0.0985 |
| 27 | 0.0033 |
| 28 | 0.0812 |
| 29 | 0.0332 |
| 30 | 0.0037 |
| 31 | 0.008 |
| 32 | 0.0072 |
| 33 | 0.0516 |
| 34 | 0.0017 |
| 35 | 0.2643 |
| 36 | 0.0346 |
| 37 | 0.169 |
| 38 | 0.133 |
| 39 | 0.1145 |
| 40 | 0.0237 |
| 41 | 0.0118 |
| 42 | 0.3628 |
| 43 | 0.1669 |
| 44 | 0.047 |
| 45 | 0.3278 |
| 46 | 0.0034 |

General Procedures

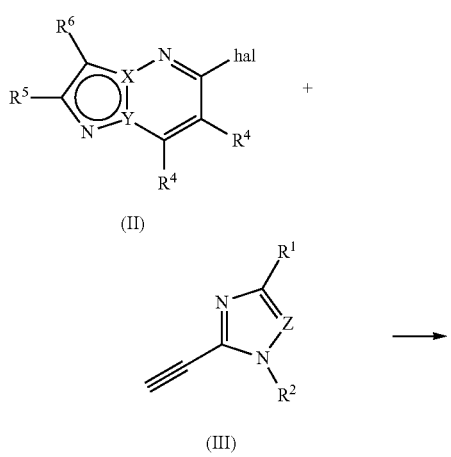

Scheme 1: Alkynes (II)

(III)

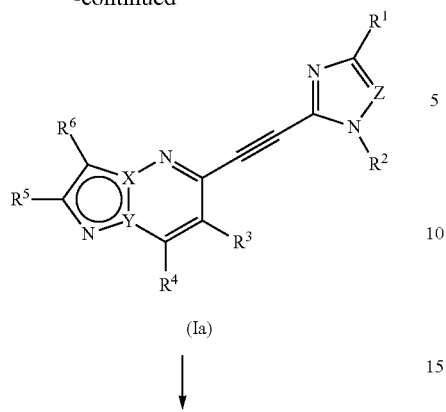
(Ia)
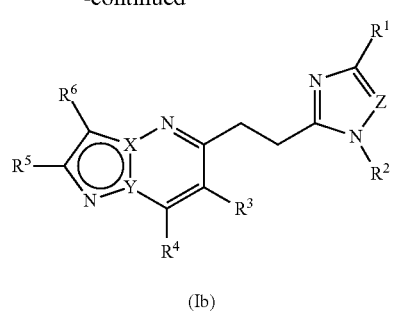
(Ib)
Scheme 2: Alkenes
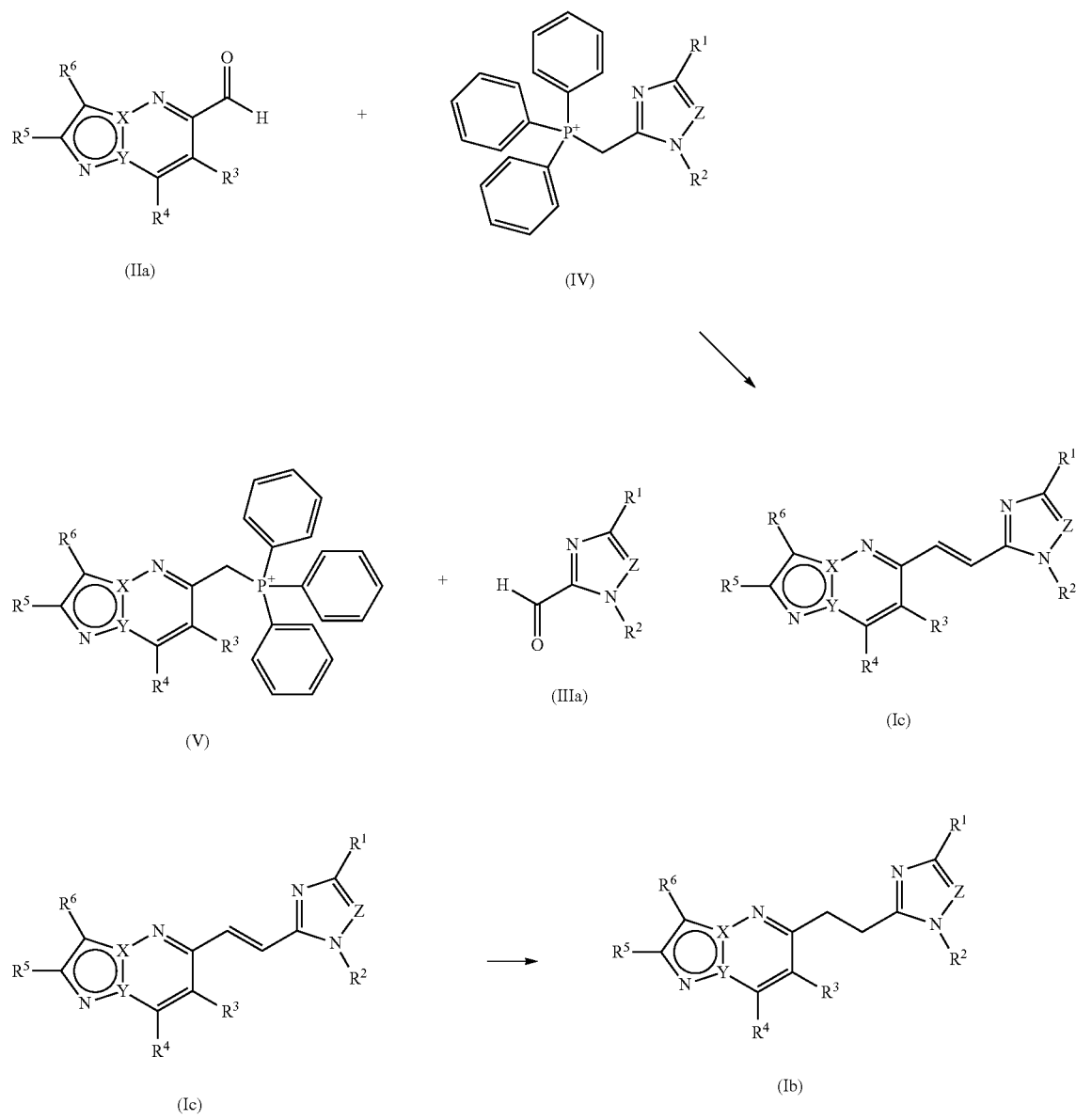

Scheme 3: Ethers

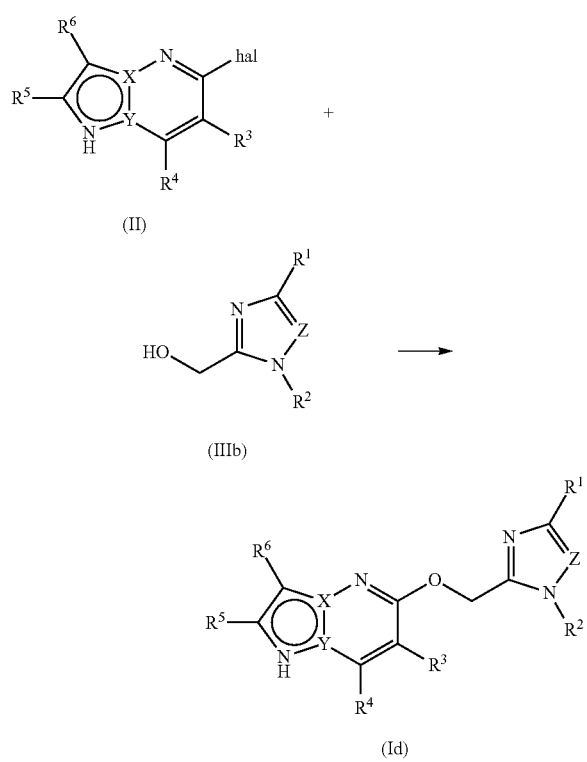

EXPERIMENTAL PART

Preparation of Intermediates

Example A.1

2-Ethynyl-1-methyl-4-phenyl-1H-imidazole

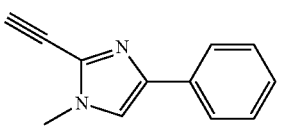

To a stirred mixture of 1-methyl-4-phenyl-1H-imidazole-2-carbaldehyde (CAS 123511-51-3; 200 mg, 1.1 mmol) and potassium carbonate (297 mg, 2.15 mmol) at r.t. in methanol (15 ml) under an argon atmosphere was added dimethyl 1-diazo-2-oxopropylphosphonate (248 mg, 1.3 mmol) in one portion. Stirring at r.t. was then continued for 4 hrs. The mixture was diluted with Et$_2$O and washed with 5% aq. KHCO$_3$. The aqueous phase was back extracted with Et$_2$O. The combined organics were washed with brine, dried over MgSO$_4$, filtered and concentrated. The crude product was purified by column chromatography using a CH$_2$Cl$_2$/MeOH gradient as eluent to provide the title compound (176 mg, 90%) as off-white solid. MS (m/e): 369.4 (M+H+)$^+$.

Example A.2

(1-Methyl-4-phenyl-imidazol-2-yl)methyl-triphenyl-phosphonium chloride hydrochloride

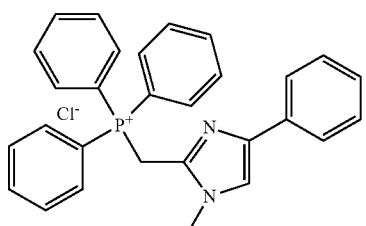

Step 1:
2-(Chloromethyl)-1-methyl-4-phenyl-1H-imidazole hydrochloride

To a stirred, cooled (0° C.) slurry of (1-methyl-4-phenyl-1H-imidazol-2-yl)methanol (CAS 675148-45-5; 2.4 g, 12.8 mmol) in dichloromethane (25 ml) under an argon atmosphere was added dropwise a solution of thionyl chloride (3.05 g, 1.9 ml, 25.7 mmol) in dichloromethane (15 ml). When the addition was complete, the ice bath was removed and the mixture was stirred at r.t. for 2 hrs, then concentrated to leave a light brown solid. This residue was triturated in Et2O/CH$_2$Cl$_2$ 1:1 (40 ml). The suspension was stirred at r.t. for 30 min. The product was collected by filtration, washed with Et$_2$O and dried to give the title compound (3.06 g, 98%) as off-white solid.

Step 2: (1-Methyl-4-phenyl-imidazol-2-yl)methyl-triphenyl-phosphonium chloride hydrochloride A suspension of 2-(chloromethyl)-1-methyl-4-phenyl-1H-imidazole hydrochloride (3.05 g, 12.5 mmol) in ethanol (25 ml) and THF (25 ml) under an argon atmosphere was added triphenylphosphine (3.27 g, 12.5 mmol) and heated to 70° C. for 18 hrs. The mixture was cooled to r.t. whereby a solid started to precipitate. The product was collected by filtration, washed with Et$_2$O and dried to obtain the title compound (3.99 g, 63%) as off-white solid. MS (m/e): 433.3

Example A.3

((1-Methyl-3-phenyl-1H-1,2,4-triazol-5-yl)methyl)triphenylphosphonium chloride hydrochloride

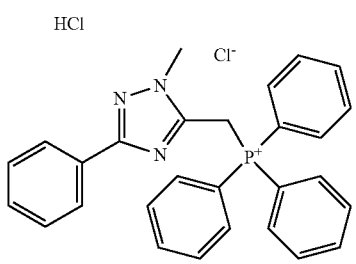 [SMILES: Cl ; Cn1nc(-c2ccccc2)nc1C[P+](c1ccccc1)(c1ccccc1)c1ccccc1 ; [Cl-]]

In analogy to the procedures described for the synthesis of example A.2, the title compound was prepared from (1-methyl-3-phenyl-1H-1,2,4-triazol-5-yl)methanol (CAS 26254-08-0). White powder. MS (m/e): 434.4 (M)+.

Example A.4

((4-Bromo-1-methyl-1H-imidazol-2-yl)methyl)triphenylphosphonium chloride hydrochloride

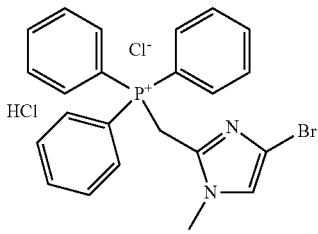 [SMILES: Cl ; Cn1cc(Br)nc1C[P+](c1ccccc1)(c1ccccc1)c1ccccc1 ; [Cl-]]

Step 1:
4-Bromo-2-(chloromethyl)-1-methyl-1H-imidazole hydrochloride

To a stirred solution of (4-bromo-1-methyl-1H-imidazol-2-yl)methanol (CAS 445303-73-1; 1.34 g, 7.0 mmol) in CH$_2$Cl$_2$ (15 ml) at 0° under an argon atmosphere was added at 0° under an argon atmosphere dropwise a solution of sulfurous dichloride (1.67 g, 1 ml, 14.0 mmol) in CH$_2$Cl$_2$ (6 ml). The mixture was stirred at 0° for 30 min and at r.t for 2 hrs, then the solvent was evaporated to provide the product (1.725 g, quant.) as white solid. MS (m/e): 209 (M).

Step 2: ((4-Bromo-1-methyl-1H-imidazol-2-yl)methyl)triphenylphosphonium chloride hydrochloride To a stirred suspension of 4-bromo-2-(chloromethyl)-1-methyl-1H-imidazole hydrochloride (1.7 g, 7.0 mmol) in ethanol (15 ml) and THF (15 ml) was added at r.t. under an argon atmosphere triphenylphosphine (1.84 g, 7.0 mmol). The mixture was stirred at 75° overnight. Then, the solvent was evaporated. The residue was triturated with Et$_2$O, filtered and dried to provide the title compound (2.64 g, 74%) as white solid. MS (m/e): 437.3 (M)+.

Example B.1

5-Chloro-2,3-dimethylpyrazolo[1,5-a]pyrimidine

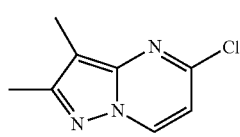

Step 1: 2,3-Dimethylpyrazolo[1,5-a]pyrimidine-5,7-diol

Sodium ethanolate 21% solution in EtOH (40.5 ml, 108 mmol) was added to ethanol (200 ml) at r.t. under an argon atmosphere. To this mixture were added diethyl malonate (4.34 g, 4.11 ml, 27.1 mmol) and 4,5-dimethyl-1H-pyrazol-3-amine hydrochloride (4 g, 27.1 mmol). The mixture was heated to 85° C. and stirring at that temperature was continued for 17 hrs. The mixture (light brown/orange suspension) was cooled to r.t. and treated with aq. 5 N HCl until pH 5 was reached. The mixture was concentrated to dryness and without further purification, the residue was used directly in the next step.

Step 2: 5, 7-Dichloro-2, 3-dimethylpyrazolo[1,5-a]pyrimidine

A mixture of 2,3-dimethylpyrazolo[1,5-a]pyrimidine-5,7-diol (4.86 g, 27.1 mmol) and N,N-dimethylaniline (5.74 g, 6 ml, 47.3 mmol) in phosphoryl trichloride (98.7 g, 60 ml, 644 mmol) was heated to 115° C. under an argon atmosphere. The brown suspension was stirred at that temperature for 3 hrs, cooled to r.t. and very carefully poured into 500 g of crushed ice. The resulting dark slurry was stirred at r.t. for 30 min and then extracted with CH$_2$Cl$_2$. The combined organics were washed with H$_2$O and brine, dried over MgSO$_4$, filtered and concentrated. The crude product was purified by silica gel chromatograph using a n-heptane/EtOAc gradient to provide the title compound (2.63 g, 45%) as light yellow solid. MS (m/e): 261.1 (M+H+)

Step 3: 5-Chloro-2, 3-dimethylpyrazolo[1,5-a]pyrimidine

To a stirred suspension of 5,7-dichloro-2,3-dimethylpyrazolo[1,5-a]pyrimidine (2.6 g, 12.1 mmol) in acetic acid (50 ml) was added portion wise at r.t. under an argon atmosphere zinc dust (3.16 g, 48.3 mmol) in one portion. Stirring at r.t. was continued for 2 days. The white compact slurry was concentrated to dryness to leave a light brown solid which was suspended in H$_2$O and slowly treated with 15% aqueous KHCO$_3$ solution. The mixture was extracted with CH$_2$Cl$_2$. The aqueous layer was back extracted with CH$_2$Cl$_2$. The combined organics were washed with brine, dried over MgSO$_4$, filtered and concentrated. The crude product was purified by column chromatography using an n-heptane/EtOAc gradient as eluent to obtain the title compound (1.66 g, 76%) as yellow solid. MS (m/e): 182.1 (M+H+)

Example B.2

6-Iodo-3-methyl-2-(trifluoromethyl)imidazo[1,2-b]pyridazine

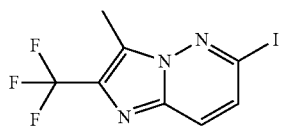

A mixture of 6-iodopyridazin-3-amine (CAS 187973-60-0; 2 g, 9.05 mmol) and 3-bromo-1,1,1-trifluorobutan-2-one (2.41 g, 11.8 mmol) in ethanol (40 ml) under an argon atmosphere was heated to 85° C. and stirred for 18 hrs. The brown solution was cooled to r.t. and concentrated to leave a brown orange sticky paste which was triturated with a mixture of 10% aq. Na$_2$CO$_3$ (20 ml) and EtOH (20 ml). The suspension was stirred at r.t. for 30 min. The product was collected by filtration, washed with H$_2$O and dried.

Example B.3

(2-Cyclopropyl-6-iodoimidazo[1,2-b]pyridazin-3-yl)methanol

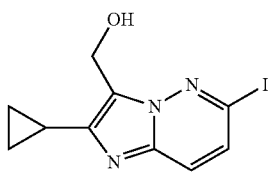 [SMILES: OCc1c(C2CC2)nc2ccc(I)nn12]

Step 1: 2-Cyclopropyl-6-iodoimidazo[1,2-b]pyridazine

A mixture of 6-iodopyridazin-3-amine (CAS 187973-60-0; 5 g, 22.6 mmol) and 2-bromo-1-cyclopropylethanone (3.69 g, 22.6 mmol) in 1,2-dimethoxyethane (80 ml) was refluxed under an argon atmosphere for 48 hrs. After cooling to r.t, the solvent was evaporated. The crude product was taken up in water and extracted with EtOAc. The organics were dried over MgSO₄, filtered and evaporated. The aqueous layer was neutralized by addition of 1N NaOH and then was extracted with CH₂Cl₂. The organics were dried over MgSO₄, filtered and evaporated. Both organic extracts were combined and purified by chromatography on silica gel using a CH₂Cl₂/MeOH gradient as eluent to provide the title compound (4.68 g, 73%) as off-white solid. MS (m/e): 207.3 (M+H)⁺.

Step 2: 2-Cyclopropyl-6-iodoimidazo[1,2-b]pyridazine-3-carbaldehyde

A mixture of 2-cyclopropyl-6-iodoimidazo[1,2-b]pyridazine (4.68 g, 16.4 mmol) and hexa-methylenetetramine (23.0 g, 164 mmol) in TFA (120 ml) were heated at 60° under an argon atmosphere for 3 days. After cooling to r.t the solvent was evaporated. The residue was dissolved in CH₂Cl₂ and washed with water. The aqueous layer was extracted with CH₂Cl₂. The combinated organics were dried over MgSO₄, filtered and evaporated. The crude product was purified by chromatography on silica gel using an heptane/EtOAc gradient as eluent to provide the title compound (3.126 g, 61%) as yellow solid. MS (m/e): 313.9 (M+H)⁺.

Step 3: (2-Cyclopropyl-6-iodoimidazo[1,2-b]pyridazin-3-yl)methanol

To a suspension of 2-cyclopropyl-6-iodoimidazo[1,2-b]pyridazine-3-carbaldehyde at r.t. under an Argon atmosphere (3.12 g, 9.97 mmol, Eq: 1.00) in MeOH (200 ml) was added portionwise NaBH4 (490 mg, 13.0 mmol). The solution was stirred at r.t for 90 min. The solvent was evaporated. The residue was taken up with water (200 ml), extracted with CH2Cl2/MeOH 9:1 (800 ml). The combined organics were dried over MgSO₄, filtered and evaporated. The yellow solid was stirred for 30 min in 200 ml Et₂O, filtered and dried to provide the title compound (2.49 g, 79%) as light yellow solid. MS (m/e): 316.0 (M+H)⁺.

Example B.4

2-(Difluoromethyl)-6-iodo-3-methylimidazo[1,2-b]pyridazine

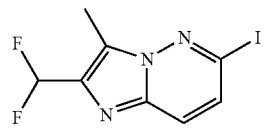

Step 1: Methyl 6-iodo-3-methylimidazo[1,2-b]pyridazine-2-carboxylate

To a solution of 6-iodopyridazin-3-amine (CAS 187973-60-0; 2 g, 9.05 mmol) in DME (100 ml) was added at r.t under an argon atmosphere methyl 3-bromo-2-oxobutanoate (2.35 g, 10.9 mmol). The reaction mixture was refluxed for 18 hrs. The solvent was removed. The crude product was purified by silica gel chromatography using a CH₂Cl₂/MeOH gradient as eluent to provide the title compound (1.3 g, 45%) as off-white solid. MS (m/e): 318.0 (M+H)⁺.

Step 2: 6-Iodo-3-methylimidazo[1,2-b]pyridazine-2-carboxylic acid

To a solution of methyl 6-iodo-3-methylimidazo[1,2-b]pyridazine-2-carboxylate (1.4 g, 4.42 mmol) in THF (70 ml) was added at 0° C. under an argon atmosphere a solution of LiOH monohydrate (556 mg, 13.2 mmol) in water (30 ml). The mixture was stirred at r.t overnight. The solvent was removed. The crude product was diluted with water and washed with EtOAc. The aqueous layer was acidified at 0° with 1 N HCl and extracted with EtOAc. The organic layer was dried over MgSO₄, filtered and evaporated to obtain the title compound (1.1 g, 82%) as off-white solid. MS (m/e): 304.1 (M+H)⁺.

Step 3: (6-Iodo-3-methylimidazo[1,2-b]pyridazin-2-yl)methanol

To a stirred, cooled at 0° mixture of 6-iodo-3-methylimidazo[1,2-b]pyridazine-2-carboxylic acid (0.5 g, 1.65 mmol) and N-methylmorpholine (250 mg, 272 µl, 2.47 mmol) in tetrahydrofuran (10 ml) under an argon atmosphere was added dropwise a solution of isobutyl carbonochloridate (315 mg, 302 µl, 2.31 mmol) in tetrahydrofuran (5 ml). After stirring at 0° C. for 30 min, sodium borohydride (125 mg, 3.3 mmol) was added portion wise and stirring at 0° C. was continued for 30 min. The mixture was stirred at r.t overnight. After careful addition of H₂O (4 ml), the mixture was allowed to warm to r.t. with stirring. The mixture was concentrated to dryness. The residual light yellow sticky solid was taken up in CH₂Cl₂/MeOH 9:1; the precipitate was removed by filtration. The filtrate was concentrated. The crude product was purified by silica gel chromatopraphy using a CH₂Cl₂/MeOH gradient as eluent to provide the title compound (0.115 g, 24%) as yellow solid. MS (m/e): 290.0 (M+H)⁺.

Step 4: 6-Iodo-3-methylimidazo[1,2-b]pyridazine-2-carbaldehyde

To a solution of (6-iodo-3-methylimidazo[1,2-b]pyridazin-2-yl)methanol (0.11 g, 381 µmol) in chloroform (15 ml) was added at r.t under an argon atmosphere manganese(IV) oxide (191 mg, 1.98 mmol). The mixture was refluxed overnight. After cooling to r.t, the mixture was filtered, washed with $CH_2Cl_2$ and concentrated to provide the title compound (97 mg, 89%) as off-white solid. MS (m/e): 288.0 $(M+H)^+$.

Step 5: 5-(Difluoromethyl)-6-iodo-3-methylimidazo[1,2-b]pyridazine

To a solution of 6-iodo-3-methylimidazo[1,2-b]pyridazine-2-carbaldehyde (95 mg, 331 µmol) in dichloromethane (5 ml) was added at r.t. under an argon atmosphere diethylaminosulfur trifluoride (201 mg, 165 µl, 1.25 mmol). The mixture was stirred at r.t overnight, then poured into a cooled and saturated $NaHCO_3$ solution, extracted with $CH_2Cl_2$, washed with brine, dried over $MgSO_4$, filtered and evaporated. The crude product was purified by silica gel chromatography using a $CH_2Cl_2$/MeOH gradient to provide the title compound (69 mg, 68%) as off-white solid). MS (m/e): 310.3 $(M+H)^+$.

Example B.5

6-Iodo-2-(trifluoromethyl)imidazo[1,2-b]pyridazine

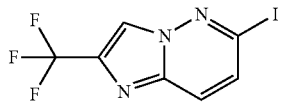 [SMILES: FC(F)(F)c1cn2nc(I)ccc2n1]

A suspension of 6-iodopyridazin-3-amine (2 g, 9.05 mmol) in ethanol (25 ml) was treated under an argon atmosphere with 3-bromo-1,1,1-trifluoropropan-2-one (2.39 g, 1.3 ml, 12.5 mmol) and stirred overnight at 85° C. The mixture was cooled to r.t., then treated with 10% $Na_2CO_3$ solution (25 ml) and stirred for 45 min. The precipitate was filtered off and dried, providing the title compound (0.89 g, 31%) as off-white solid. MS (m/e): 314.2 $(M+H)^+$.

Example B.6

6-Chloro-3-methyl-imidazo[1,2-b]pyridazine-2-carbonitrile

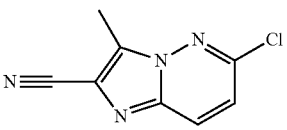

Step 1: 6-Chloro-3-methyl-imidazo[1,2-b]pyridazine-2-carboxylic acid amide

To a solution of 6-chloro-3-methyl-imidazo[1,2-b]pyridazine-2-carboxylic acid methyl ester (described in step 1 of example B.4; 1.5 g, 6.7 mmol) in acetonitrile (20 ml) in a sealed tube was added aqueous ammonia (28%; 100 ml), and the reaction mass was stirred at 100° C. for 10 hrs. The reaction mixture was diluted with water (50 ml) and extracted with EtOAc. The combined organics were washed with water and brine, dried over anhydrous $Na_2SO_4$ filtered, and concentrated. The crude product was purified by trituration with a mixture of $CH_2Cl_2$ and hexane, filtered and dried to give the title compound (0.7 g, 50%) as pale yellow solid. LC-MS (ESI): 212.2

Step 2: 6-Chloro-3-methyl-imidazo[1,2-b]pyridazine-2-carbonitrile

To a solution of 6-chloro-3-methyl-imidazo[1,2-b]pyridazine-2-carboxylic acid amide (1.65 g, 7.8 mmol) in pyridine (4.8 ml) was added trifluoro acetic anhydride (1.65 ml, 11.8 mmol) at 10° C., and the mixture was stirred for 30 min at 10° C. followed by another 30 min at 25° C. The reaction mixture was diluted with water (5 ml), acidified (pH 1 to 2) with aqueous HCl (3N). The resultant precipitated solid was filtered and dried to give the title compound (1.3 g, 86%) as white solid. LC-MS (ESI): 193.0

Example B.7

2-Cyclopropyl-6-iodo-3-methyl-imidazo[1,2-b]pyridazine

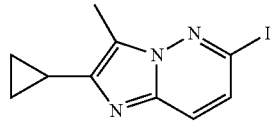

A mixture of 2-bromo-1-cyclopropylpropan-1-one (0.72 g, 2.03 mmol) and 6-iodopyridazin-3-amine (449 mg, 2.03 mmol) in 1,2-dimethoxyethane (10 ml) was refluxed under an argon atmosphere for 20 hrs. After cooling to r.t, the solvent was evaporated. The crude product was taken up in water (15 ml) and extracted with EtOAc The organics were dried over $MgSO_4$, filtered and evaporated. The aqueous layer was neutralized by addition of 1N NaOH and then extracted extracted with $CH_2Cl_2$. The organic layer was dried over $MgSO_4$, filtered and evaporated. The two organic extracts were combinated and concentrated. The crude product was purified by silica gel chromatography using a heptane/EtOAc gradient as eluent to provide the title compound (30 mg, 5%; not clean) as light brown solid. MS (m/e): 300.3 $(M+H)^+$.

Example B.8

2,3-Dimethylimidazo[1,2-b]pyridazine-6-carbaldehyde

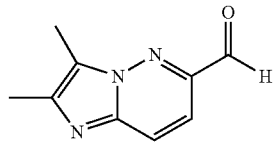

Step 1: 2,3-Dimethyl-6-vinylimidazo[1,2-b]pyridazine

To a stirred solution of 6-chloro-2,3-dimethylimidazo[1,2-b]pyridazine (CAS 17412-26-9; 616 mg, 3.39 mmol) and tributyl(vinyl)stannane (1.13 g, 3.56 mmol) at r.t. in DMF (10 ml) under an argon atmosphere was added Pd(Ph₃P)₄ (588 mg, 509 μmol). The mixture was evacuated and back filled with argon before it was heated to 120° C. overnight, then cooled to r.t., taken up with saturated aqueous NH₄Cl and extracted with EtOAc (40 ml). The aqueous phase was extracted with EtOAc. The combined organics were washed with H₂O and brine, dried over MgSO₄, filtered and concentrated. The crude product was purified by silica gel chromatography using a CH₂Cl₂/MeOH gradient as eluent. The resulting product was still contaminated by triphenylphosphine oxide. Therefore it was purified a second time on Isolute® Flash-NH₂ silica gel (from Separtis) using a heptane/EtOAc gradient as eluent, providing the title compound (340 mg, 60%) as light yellow solid. MS (m/e): 174.3 (M+H)⁺.

Step 2: 2,3-Dimethylimidazo[1,2-b]pyridazine-6-carbaldehyde

To a mixture of 2,3-dimethyl-6-vinylimidazo[1,2-b]pyridazine (330 mg, 1.91 mmol) and osmium(VIII) oxide 4% solution in H₂O (605 mg, 95.3 μmol) was added at r.t. under an argon atmosphere a solution of 4-methylmorpholine 4-oxide (335 mg, 2.86 mmol) in acetone (12 ml) and water (1 ml). The mixture (clear light yellow solution) was heated to 45° C. for 4 hrs, then concentrated. The residue was taken up in THF (20 ml) and water (4.5 ml). Sodium periodate (815 mg, 3.81 mmol) was then added and the mixture was stirred at 45° C. for 16 hrs, the solution soon turning to a compact yellow suspension. The mixture was cooled to r.t., quenched by the addition of 10% aq. Na₂SO₃ (30 ml) and extracted with CH₂Cl₂. The combined organics were washed with brine, dried over MgSO₄, filtered and concentrated. The crude product was purified by silica gel chromatography using an CH₂Cl₂/MeOH gradient as eluent to provide the title compound (280 mg, 84%) as yellow solid. MS (m/e): 176.1 (M+H)⁺.

Example B.9

6-Formyl-3-methyl-imidazo[1,2-b]pyridazine-2-carbonitrile

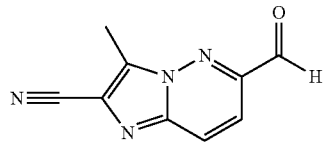

Step. 1: 3-Methyl-6-vinyl-imidazo[1,2-b]pyridazine-2-carbonitrile

To a solution of 6-chloro-3-methylimidazo[1,2-b]pyridazine-2-carbonitrile (described in example B.6; 0.5 g, 2.6 mmol) and tributyl(vinyl)stannane (864 mg, 2.73 mmol) in DMF (10 ml) was added at r.t. under an argon atmosphere Pd(Ph₃)₄ (450 mg, 389 μmol). The mixture was evacuated and back filled with argon, then it was heated at 120° overnight. The mixture cooled to r.t., treated with saturated aqueous NH₄Cl and extracted with EtOAc. The aqueous layer was extracted with EtOAc. The combined organics were washed with H₂O, brine and dried over MgSO₄, filtered and concentrated. The crude product was purified by silica gel chromatography using a heptane/EtOAc gradient as eluent to provide the title compound (0.2 g, 42%) as yellow solid. MS (m/e): 185.1 (M+H)⁺.

Step 2: 6-Formyl-3-methyl-imidazo[1,2-b]pyridazine-2-carbonitrile

To a mixture of 3-methyl-6-vinylimidazo[1,2-b]pyridazine-2-carbonitrile (0.2 g, 1.09 mmol, Eq: 1.00) and osmium(VIII) oxide (345 mg, 54.3 μmol) was added at r.t. and an argon atmosphere a solution of 4-methylmorpholine 4-oxide hydrate (220 mg, 1.63 mmol) in acetone (12 ml) and water (1 ml). The mixture (clear light yellow solution) was heated to 45° C. for 4 hrs, then concentrated. The residue was taken up in THF (20 ml) and water (4.5 ml). sodium periodate (464 mg, 2.17 mmol) was added and the mixture was stirred at 45° C. for 16 hrs (the mixture soon turning to a compact yellow suspension). The mixture was cooled to r.t. and quenched by the addition of 10% aq. Na₂SO₃ (40 ml). This was extracted with CH₂Cl₂, dried over MgSO₄, filtered and concentrated. The crude product was purified by silica gel chromatography using CH₂Cl₂/MeOH gradient as eluent to obtain the title compound (0.16 g, 79%) as off white solid. MS (m/e): 187.1 (M+H)⁺.

Example B.10

3,8-dimethyl-2-(trifluoromethyl)imidazo[1,2-b]pyridazine-6-carbaldehyde

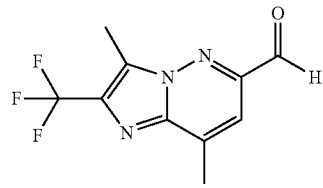 [SMILES: Cc1cc(C=O)nn2c(C)c(C(F)(F)F)nc12]

Step 1: 6-Chloro-3, 8-dimethyl-2-trifluoromethyl-imidazo[2-b]pyridazine

A mixture of 6-chloro-4-methyl-pyridazin-3-ylamine (CAS 64068-00-4) along with its isomer (5.0 g, 34.8 mmol) and 3-bromo-1, 1, 1-trifluoro-2-butanone (5.2 ml, 41.8 mmol) in dimethoxyethane (200 ml) was refluxed under argon for 18 hrs, then concentrated. The crude product was purified by silica gel chromatography using 5% EtOAc in hexane as eluent to obtain the title compound (2.0 g, 23%) as off white solid. LC-MS (ESI): 250 (M+H).

Step 2: 3, 8-Dimethyl-2-trifluoromethyl-6-vinyl-imidazo[1,2-b]pyridazine

A solution of 6-chloro-3, 8-dimethyl-2-trifluoromethyl-imidazo[1, 2-b]pyridazine (8.0 g, 32.1 mmol) in DMF (50 ml) was evacuated and refilled with argon repeatedly during 10 min. To this mixture were then added tributyl (vinyl) stannane (11.3 ml, 38.5 mmol) and tetrakis(triphenylphosphine)palladium(0) (1.8 g, 1.6 mmol) at 25° C. The mixture was again evacuated and refilled repeatedly with argon during 10 min and then heated to 80° C. for 5 hrs. The mixture was cooled to 25° C., diluted with water extracted with EtOAc. The combined organics were washed with ice cold water and brine, dried over anhydrous Na₂SO₄, filtered and concentrated. The crude product was purified by silica gel chromatography using 10% EtOAc in hexane as eluent to give the title compound (5.0 g, 64%) as off-white solid. LC-MS (ESI): 242 (M+H).

Step 3: 3, 8-Dimethyl-2-trifluoromethyl-imidazo[2-b]pyridazine-6-carbaldehyde To a mixture of 3,8-dimethyl-2-trifluoromethyl-6-vinyl-imidazo[1,2-b]pyridazine ((5.0 g, 20.7 mmol) and osmium tetroxide (4% solution in water, 0.5 ml, 2.1 mmol) at 25° C. under nitrogen was added a solution of 4-methylmorpholine 4-oxide (3.1 ml, 31.1 mmol) in acetone (150 ml) and water (15 ml). The mixture was stirred at 50° C. for 4 hrs. The solvent was removed in vacuo. The resultant residue was diluted with THF (150 ml) and water (30 ml). Sodium periodate (8.9 g, 41.5 mmol) was then added and the mixture was stirred at 50° C. for another 16 hrs. The mixture was cooled to 25° C., quenched by the addition of 10% aqueous solution of Na₂SO₃, and extracted with DCM. The combined organics were washed with brine, dried over anhydrous Na₂SO₄, filtered and concentrated. The crude material was purified by silica gel chromatography using 30% EtOAc in hexane as eluent to give the title compound (4.0 g, 79%) as off-white solid. GCMS: 243.

Example B.11

6-Formyl-N,3-dimethyl-2-(trifluoromethyl)imidazo[1,2-b]pyridazine-8-carboxamide

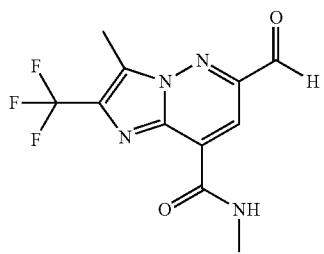 [SMILES: CNC(=O)c1cc(C=O)nn2c(C)c(C(F)(F)F)nc12]

Step 1: 3, 6-Dichloropyridazine-4-carbonyl chloride

To a stirred, cooled (0° C.) suspension of 3,6-dichloropyridazine-4-carboxylic acid (5 g, 25.9 mmol) in dichloromethane (50 ml) under an argon atmosphere was added carefully oxalyl chloride (3.62 g, 2.49 ml, 28.5 mmol) followed by DMF (4 drops). Stirring at r.t. was then continued at r.t. overnight. The reaction mixture was concentrated and directly used in the next step without further purification.

Step 2: 3, 6-dichloro-N-methylpyridazine-4-carboxamide

To a stirred, cooled (0° C.) solution of the crude 3,6-dichloropyridazine-4-carbonyl chloride (5.39 g, 25.5 mmol) in dichloromethane (80 ml) were added under an argon atmosphere methylamine hydrochloride (3.44 g, 51.0 mmol) and triethylamine (5.16 g, 7.11 ml, 51.0 mmol). The mixture was then stirred at r.t. overnight. The insoluble material was filtered off and washed with CH₂Cl₂. The dark brown filtrate was concentrated. The crude product was purified by silica gel chromatography using a CH₂Cl₂/MeOH gradient as eluent to provide the title compound (2.93 g, 56%) as light brown solid. MS (m/e): 206.1 (M+H)⁺.

Step 3: 3-Amino-6-chloro-N-methylpyridazine-4-carboxamide

To a stirred suspension of 3,6-dichloro-N-methyl-pyridazine-4-carboxamide (2.85 g, 13.8 mmol) in conc. NH₄OH (25 ml) was heated in an autoclave at 120° C. overnight. The mixture was cooled to r.t. and concentrated to leave a yellow solid. The residue was taken up in CH₂Cl₂/MeOH 1:1 (70 ml) whereupon a precipitate formed. The solid was removed by filtration. The filtrate was concentrated and the residue was purified by silica gel chromatography using a CH₂Cl₂/MeOH gradient as eluent to obtain the title compound (325 mg, 13%) as yellow solid. MS (m/e): 187.2 (M+H)⁺.

Step 4: 6-Chloro-2-hydroxy-N,3-dimethyl-2-(trifluoromethyl)-2,3-dihydroimidazo[1,2-b]pyridazine-8-carboxamide A mixture of 3-amino-6-chloro-N-methylpyridazine-4-carboxamide (320 mg, 1.71 mmol), 3-bromo-1,1,1-trifluorobutan-2-one (457 mg, 2.23 mmol) and sodium bicarbonate (187 mg, 2.23 mmol) in ethanol (15 ml) was stirred at 80° C. under an argon atmosphere overnight. The mixture was evaporated. The crude product was purified by silica gel chromatography using a CH₂Cl₂/MeOH gradient as eluent to provide the title compound (368 mg, 69%) as yellow solid. MS (m/e): 311.4 (M+H)⁺.

Step 5: 6-Chloro-N,3-dimethyl-2-(trifluoromethyl)imidazo[1,2-b]pyridazine-8-carboxamide To a mixture of 6-chloro-2-hydroxy-N,3-dimethyl-2-(trifluoromethyl)-2,3-dihydroimidazo[1,2-b]pyridazine-8-carboxamide (380 mg, 1.22 mmol) and pyridine (194 mg, 198 µl, 2.45 mmol) in THF (10 ml) was added at 0° C. under an argon atmosphere sulfurous dichloride (291 mg, 177 µl, 2.45 mmol). The mixture was stirred at r.t. overnight. The mixture was poured into 50 ml ice water and extracted with CH₂Cl₂. The combined organics were washed with H₂O, dried over MgSO₄, filtered and evaporated to obtain the title compound (360 mg, quant.) as yellow solid. MS (m/e): 293.3 (M+H)⁺.

Step 6: N,3-Dimethyl-2-(trifluoromethyl)-6-vinylimidazo[1,2-b]pyridazine-8-carboxamide To a stirred solution of 6-chloro-N,3-dimethyl-2-(trifluoromethyl)imidazo[1,2-b]pyridazine-8-carboxamide (0.36 g, 1.23 mmol) and tributyl(vinyl)stannane (255 mg, 235 µl, 805 µmol) in DMF (8 ml) under an argon atmosphere was added tetrakis(triphenylphosphine) palladium(0) (213 mg, 185 µmol). The mixture was evacuated and back-filled with argon before it was heated to 120° C. overnight. After cooling to r.t, the mixture was diluted with EtOAc, and the insoluble materials were filtered off. The filtrate was washed with H₂O and brine, dried over MgSO₄, filtered and evaporated. The crude product was purified using a heptane/EtOAc gradient as an eluent to provide the title compound (157 mg, 45%) as off-white solid. MS (m/e): 465.5 (M+H)⁺.

Step 7: 6-Formyl-N,3-dimethyl-2-(trifluoromethyl)imidazo[1,2-b]pyridazine-8-carboxamide To a mixture of N,3-dimethyl-2-(trifluoromethyl)-6-vinylimidazo[1,2-b]pyridazine-8-carboxamide (0.155 g, 545

μmol) and osmium(VIII) oxide (173 mg, 27.3 μmol) was added at r.t. under an argon atmosphere a solution of 4-methylmorpholine 4-oxide (95.8 mg, 818 μmol) in acetone (3 ml) and water (0.27 ml). The mixture was stirred at 45° C. for 4 hrs. The solvent was removed and the residue was taken up in THF (4.6 ml) and water (1.15 ml). Sodium periodate (233 mg, 1.09 mmol) was added and the mixture was stirred at 45° C. for 16 hrs. The mixture was cooled to r.t., quenched with 10% aqueous $Na_2SO_3$ and extracted with $CH_2Cl_2$. The combined organics were washed with brine, dried over $MgSO_4$, filtered and concentrated. The crude product was purified by silica gel chromatography using a $CH_2Cl_2$/MeOH gradient as eluent to obtain the title compound (103 mg, 66%) as yellow solid. MS (m/e): 287.1 $(M+H)^+$.

Example B.12

((2,3-Dimethylimidazo[1,2-b]pyridazin-6-yl)methyl) triphenyl-phosphonium chloride

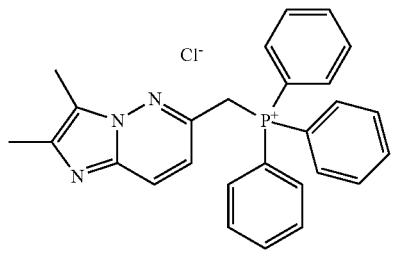 [SMILES: Cc1nc2ccc(C[P+](c3ccccc3)(c3ccccc3)c3ccccc3)nn2c1C ; [Cl-]]

Step 1: (2,3-Dimethylimidazo[1,2-b]pyridazin-6-yl) methanol

To a stirred solution of 2,3-dimethylimidazo[1,2-b]pyridazine-6-carbaldehyde (example B.8; 1.05 g, 5.99 mmol) in MeOH (25 ml) and $CH_2Cl_2$ (25 ml) was added at r.t under an argon atmosphere in one portion $NaBH_4$ (454 mg, 12.0 mmol). The mixture was stirred at r.t for 2 hrs. The mixture was diluted with $CH_2Cl_2$ and washed with water. The aqueous layer was extracted with $CH_2Cl_2$. The combined organics were dried over $MgSO_4$, filtered and evaporated. by silica gel chromatography using a $CH_2Cl_2$/MeOH gradient as eluent to obtain the title compound (645 mg, 61%) as white solid. MS (m/e): 178.3 $(M+H)^+$.

Step 2: 6-(Chloromethyl)-2, 3-dimethylimidazo[1, 2-b]pyridazine

To a stirred suspension of (2,3-dimethylimidazo[1,2-b]pyridazin-6-yl)methanol (0.645 g, 3.64 mmol) in $CH_2Cl_2$ (25 ml) was drop wise added at 0° under an argon atmosphere a solution of sulfurous dichloride (853 mg, 0.523 mL, 7.17 mmol) in $CH_2Cl_2$ (10 ml). The ice bath was removed and the solution was stirred at r.t 90 min. The mixture was evaporated to dryness to provide the title compound (830 mg, quant.) as white solid. MS (m/e): 196.2 $(M+H)^+$.

Step 3: ((2,3-Dimethylimidazo[1,2-b]pyridazin-6-yl) methyl)triphenyl-phosphonium chloride A mixture of 6-(chloromethyl)-2,3-dimethyl-7,8-dihydroimidazo[1,2-b]pyridazine (0.82 g, 4.15 mmol) and triphenylphosphine (1.09 g, 4.15 mmol) in ethanol (25 ml) and tetrahydrofuran (25 ml) was stirred at 70° under an argon atmosphere overnight. The mixture was cooled to r.t and evaporated to dryness to provide the title compound (2 g, quant.) as light yellow solid which was used without further purification. MS (m/e): 422.6 $(M+H)^+$.

Example B.13

6-Chloro-8-methoxy-3-methyl-2-(trifluoromethyl) imidazo[1,2-b]pyridazine

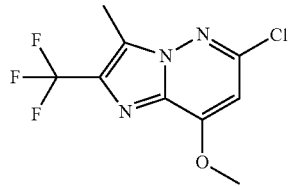 [SMILES: COc1cc(Cl)nn2c(C)c(C(F)(F)F)nc12]

A mixture of 6-chloro-4-methoxy-pyridazin-3-amine (CAS 808770-39-0; 610 mg, 3.82 mmol) and 3-bromo-1,1,1-trifluorobutan-2-one (1.02 g, 4.97 mmol) in ethanol (10 ml) under an argon atmosphere was stirred at 85° C. for 17 hrs. The mixture was cooled to r.t. and concentrated to leave a dark brown viscous oil. The residue was triturated in EtOH (7 ml) and 5% $Na_2CO_3$ (7 ml). The resulting suspension was stirred at r.t. for 1 hr. The solid was collected by filtration, washed with $H_2O$ and dried to provide the title compound (178 mg, 17%) as light brown solid. MS (m/e): 266.2 $(M+H)^+$.

DESCRIPTION OF EXAMPLES

Example 1

2,3-Dimethyl-6-((1-methyl-4-phenyl-1H-imidazol-2-yl)ethynyl)imidazo[1,2-b]pyridazine

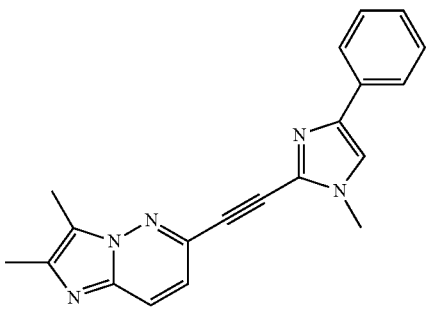 [SMILES: Cc1nc2ccc(C#Cc3nc(-c4ccccc4)cn3C)nn2c1C]

To a stirred solution of 6-chloro-2,3-dimethyl-imidazo[1,2-b]pyridazine (CAS 17412-26-9; 245 mg, 1.35 mmol) at r.t. in DMF (3 ml) under an argon atmosphere were added copper(I) iodide (2.57 mg, 13.5 μmol), triethylamine (273 mg, 374 μl, 2.7 mmol) and bis(triphenylphosphine) palladium (II) chloride (9.47 mg, 13.5 μmol). The mixture was evacuated and back filled with argon. 2-Ethynyl-1-methyl-4-phenyl-1H-imidazole (described in example A.1; 320 mg, 1.75 mmol) was added and again the mixture was evacuated and back filled with argon. The mixture was then heated to 80° C. for 8 hrs. The dark brown mixture was cooled to r.t., taken up in $H_2O$ and extracted with EtOAc. The combined organics were washed with H₂O and brine, dried over MgSO₄, filtered and concentrated. The crude product was purified twice, first by silica gel chromatography using a CH₂Cl₂/MeOH gradient as eluent, then by chromatography on Isolute® Flash-NH₂ silica gel (from Separtis) using a heptane/EtOAc gradient as eluent to provide the title compound (83 mg, 17%) as light yellow solid. MS (m/e): 328.0 (M+H)⁺.

In analogy to example 1, examples 2 to 10 of the following table were prepared by Sonogashira coupling.

| Example No. | Structure | Systematic Name | Starting materials | mass found (M + H)⁺ |
| --- | --- | --- | --- | --- |
| 2 | 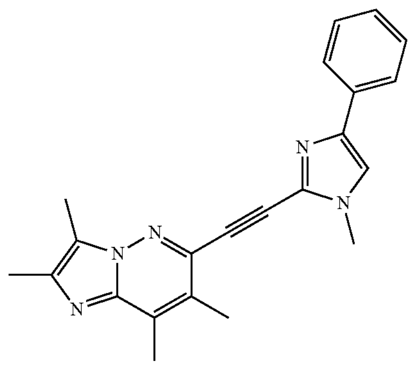 [SMILES: Cc1nc2c(C)c(C)c(C#Cc3nc(-c4ccccc4)cn3C)nn2c1C] | 2,3,7,8-Tetramethyl-6-((1-methyl-4-phenyl-1H-imidazol-2-yl)ethynyl)imidazo[1,2-b]pyridazine | 2-Ethynyl-1-methyl-4-phenyl-1H-imidazole (example A.1) and 6-chloro-2,3,7,8-tetramethyl-imidazo[1,2-b]pyridazine (CAS 17412-25-8) | 355.3 |
| 3 | 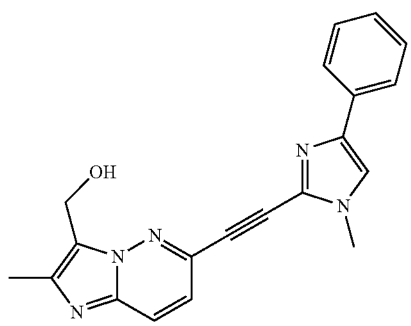 [SMILES: Cc1nc2ccc(C#Cc3nc(-c4ccccc4)cn3C)nn2c1CO] | (2-Methyl-6-((1-methyl-4-phenyl-1H-imidazol-2-yl)ethynyl)imidazo[1,2-b]pyridazin-3-yl)methanol | 2-Ethynyl-1-methyl-4-phenyl-1H-imidazole (example A.1) and (6-chloro-2-methyl-imidazo[1,2-b]pyridazin-3-yl)methanol (CAS 675580-53-7) | 344.4 |
| 4 | 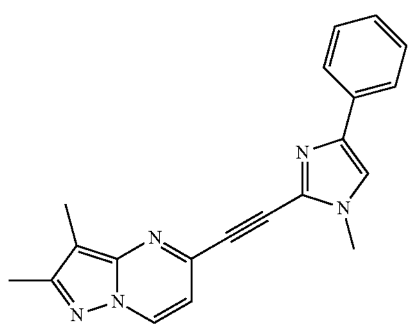 [SMILES: Cc1nn2ccc(C#Cc3nc(-c4ccccc4)cn3C)nc2c1C] | 2,3-Dimethyl-5-((1-methyl-4-phenyl-1H-imidazol-2-yl)ethynyl)pyrazolo[1,5-a]pyrimidine | 2-Ethynyl-1-methyl-4-phenyl-1H-imidazole (example A.1) and 5-chloro-2,3-dimethylpyrazolo[1,5-a]pyrimidine (example B.1) | 328.4 |
| 5 | 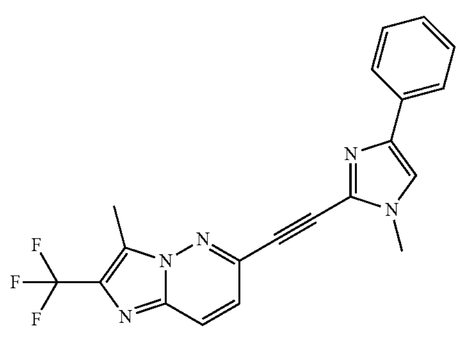 [SMILES: Cc1c(C(F)(F)F)nc2ccc(C#Cc3nc(-c4ccccc4)cn3C)nn12] | 3-Methyl-6-((1-methyl-4-phenyl-1H-imidazol-2-yl)ethynyl)-2-(trifluoromethyl)imidazo[1,2-b]pyridazine | 2-Ethynyl-1-methyl-4-phenyl-1H-imidazole (example A.1) and 6-iodo-3-methyl-2-(trifluoromethyl)imidazo[1,2-b]pyridazine (example B.2) | 382.1 |

| Example No. | Structure | Systematic Name | Starting materials | mass found (M + H)+ |
|---|---|---|---|---|
| 6 | 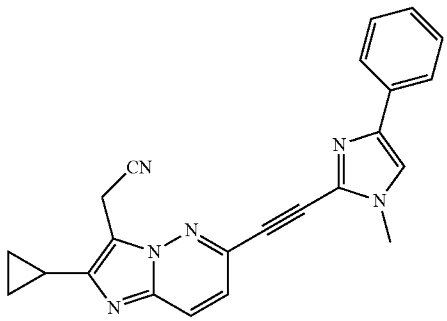 [SMILES: Cn1cc(-c2ccccc2)nc1C#Cc1ccc2nc(C3CC3)c(CC#N)n2n1] | (2-Cyclopropyl-6-((1-methyl-4-phenyl-1H-imidazol-2-yl)ethynyl)imidazo[1,2-b]pyridazin-3-yl)methanol | 2-Ethynyl-1-methyl-4-phenyl-1H-imidazole (example A.1) and (2-cyclopropyl-6-iodoimidazo[1,2-b]pyridazin-3-yl)methanol (example B.3) | 370.5 |
| 7 | 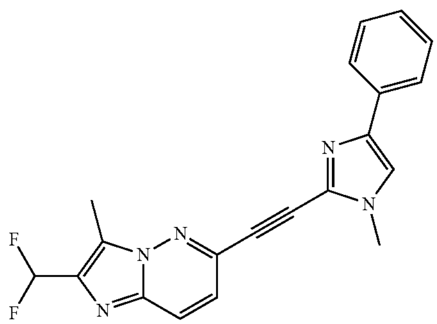 [SMILES: Cc1c(C(F)F)nc2ccc(C#Cc3nc(-c4ccccc4)cn3C)nn12] | 2-(Difluoromethyl)-3-methyl-6-((1-methyl-4-phenyl-1H-imidazol-2-yl)ethynyl)imidazo[1,2-b]pyridazine | 2-Ethynyl-1-methyl-4-phenyl-1H-imidazole (example A.1) and 2-(difluoromethyl)-6-iodo-3-methylimidazo[1,2-b]pyridazine (example B.4) | ?? |
| 8 | 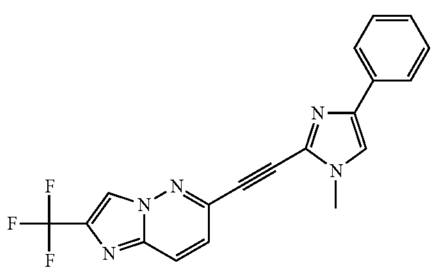 [SMILES: Cn1cc(-c2ccccc2)nc1C#Cc1ccc2nc(C(F)(F)F)cn2n1] | 6-(1-Methyl-4-phenyl-1H-imidazol-2-ylethynyl)-2-trifluoromethyl-imidazo[1,2-b]pyridazine | 2-Ethynyl-1-methyl-4-phenyl-1H-imidazole (example A.1) and 6-iodo-2-(trifluoromethyl)imidazo[1,2-b]pyridazine (example B.5) | 368.4 |
| 9 | 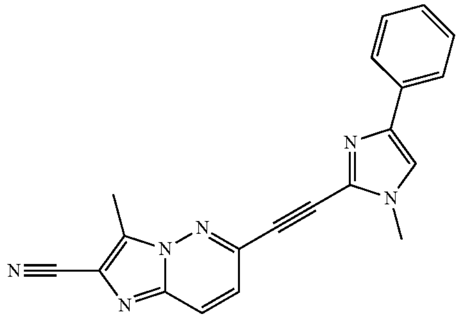 [SMILES: Cc1c(C#N)nc2ccc(C#Cc3nc(-c4ccccc4)cn3C)nn12] | 3-Methyl-6-(1-methyl-4-phenyl-1H-imidazol-2-ylethynyl)-imidazo[1,2-b]pyridazine-2-carbonitrile | 2-Ethynyl-1-methyl-4-phenyl-1H-imidazole (example A.1) and 6-chloro-3-methyl-imidazo[1,2-b]pyridazine-2-carbonitrile (example B.6) | 339.4 |

| Example No. | Structure | Systematic Name | Starting materials | mass found (M + H)+ |
|---|---|---|---|---|
| 10 | 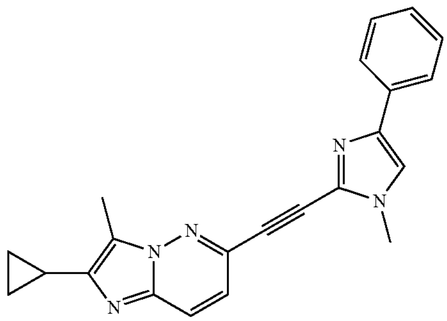 [SMILES: Cc1c(C2CC2)nc2ccc(C#Cc3nc(-c4ccccc4)cn3C)nn12] | 2-Cyclopropyl-3-methyl-6-((1-methyl-4-phenyl-1H-imidazol-2-yl)ethynyl)imidazo[1,2-b]pyridazine | 2-Ethynyl-1-methyl-4-phenyl-1H-imidazole (example A.1) and 2-cyclopropyl-6-iodo-3-methyl-imidazo[1,2-b]pyridazine (example B.7) | 354.0 |

Example 11

(E)-2,3-Dimethyl-6-(2-(1-methyl-3-phenyl-1H-1,2,4-triazol-5-yl)vinyl)imidazo[1,2-b]pyridazine

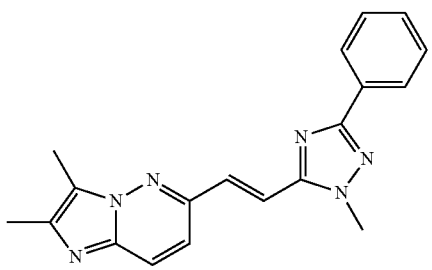 [SMILES: Cc1nc2ccc(/C=C/c3nc(-c4ccccc4)nn3C)nn2c1C]

To a stirred suspension of ((1-methyl-3-phenyl-1H-1,2,4-triazol-5-yl)methyl)triphenylphosphonium chloride hydrochloride (example A.3; 385 mg, 760 µmol) at r.t. in THF (15 ml) under were added under an argon atmosphere DBU (289 mg, 284 µl, 1.9 mmol) and 2,3-dimethylimidazo[1,2-b]pyridazine-6-carbaldehyde (example B.8; 133 mg, 760 µmol). The yellow compact suspension was stirred at r.t. for 22 hrs. The mixture was then concentrated and the residue was purified by silica gel chromatography using a CH$_2$Cl$_2$/MeOH gradient as eluent to give the title compound (189 mg, 68%). MS (m/e): 331.3 (M+H$^+$).

Compound 12 was prepared in analogy to example 11.

Example 13

2,3-Dimethyl-6-(2-(1-methyl-4-phenyl-1H-imidazol-2-yl)ethyl)imidazo[1,2-b]pyridazine

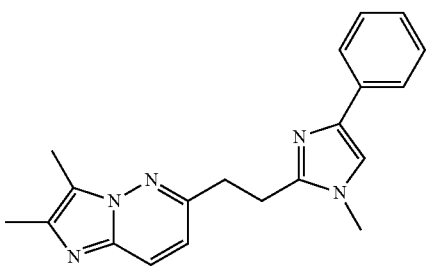 [SMILES: Cc1nc2ccc(CCc3nc(-c4ccccc4)cn3C)nn2c1C]

To a stirred suspension of 2,3-dimethyl-6-((1-methyl-4-phenyl-1H-imidazol-2-yl)ethynyl)-imidazo[1,2-b]pyridazine (example 1; 80 mg, 220 µmol) in methanol/CH$_2$Cl$_2$ 1:1 (10 ml) was added 10% Pd/C (10 mg). The black suspension was stirred at r.t. under a hydrogen atmosphere for overnight. The catalyst was filtered off and washed with MeOH. The filtrate was concentrated. The crude product was purified by silica gel chromatography using a CH$_2$Cl$_2$/MeOH gradient as eluent to obtain the title compound (65 mg, 90%) as off-white solid. MS(m/e): 332.0 (M+H)$^+$ Compounds 14-22 were prepared in analogy to example 13.

| Expl. No. | Structure | Systematic Name | Starting materials | MW found (M + H)+ |
|---|---|---|---|---|
| 12 | 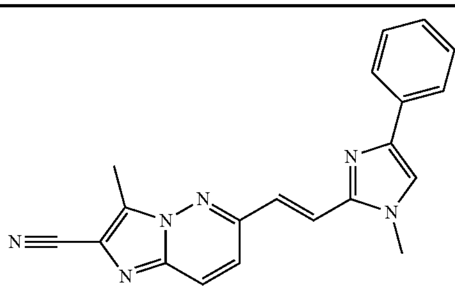 | (E)-3-methyl-6-(2-(1-methyl-4-phenyl-1H-imidazol-2-yl)vinyl)imidazo[1,2-b]pyridazine-2-carbonitrile | (1-Methyl-4-phenyl-imidazol-2-yl)methyl-triphenyl-phosphonium chloride hydrochloride (example A.2) and 6-formyl-3-methyl-imidazo[1,2-b]pyridazine-2-carbonitrile (example B.9) | 341.4 |

| Expl. No. | Structure | Systematic Name | Starting materials | MW found (MH)+ |
|---|---|---|---|---|
| 14 | 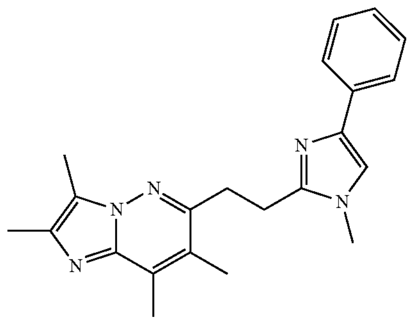 [SMILES: Cc1nc2c(C)c(C)c(CCc3nc(-c4ccccc4)cn3C)nn2c1C] | 2,3,7,8-Tetramethyl-6-(2-(1-methyl-4-phenyl-1H-imidazol-2-yl)ethyl)imidazo[1,2-b]pyridazine | 2,3,7,8-Tetramethyl-6-((1-methyl-4-phenyl-1H-imidazol-2-yl)ethynyl)imidazo[1,2-b]pyridazine (example 2) | 360.1 |
| 15 | 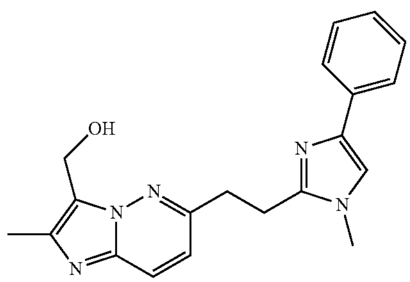 [SMILES: Cc1nc2ccc(CCc3nc(-c4ccccc4)cn3C)nn2c1CO] | (2-Methyl-6-(2-(1-methyl-4-phenyl-1H-imidazol-2-yl)ethyl)imidazo[1,2-b]pyridazin-3-yl)methanol | (2-Methyl-6-((1-methyl-4-phenyl-1H-imidazol-2-yl)ethynyl)imidazo[1,2-b]pyridazin-3-yl)methanol (example 3) | 348.5 |
| 16 | 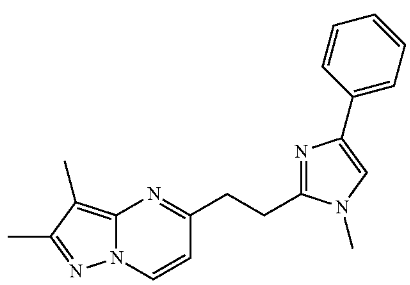 [SMILES: Cc1nn2ccc(CCc3nc(-c4ccccc4)cn3C)nc2c1C] | 2,3-Dimethyl-5-(2-(1-methyl-4-phenyl-1H-imidazol-2-yl)ethyl)pyrazolo[1,5-a]pyrimidine | 2,3-Dimethyl-5-((1-methyl-4-phenyl-1H-imidazol-2-yl)ethynyl)pyrazolo[1,5-a]pyrimidine (example 4) | 332.2 |
| 17 | 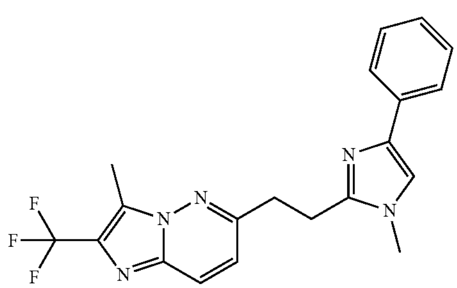 [SMILES: Cc1c(C(F)(F)F)nc2ccc(CCc3nc(-c4ccccc4)cn3C)nn12] | 3-Methyl-6-(2-(1-methyl-4-phenyl-1H-imidazol-2-yl)ethyl)-2-(trifluoromethyl)imidazo[1,2-b]pyridazine | 3-Methyl-6-((1-methyl-4-phenyl-1H-imidazol-2-yl)ethynyl)-2-(trifluoromethyl)imidazo[1,2-b]pyridazine (example 5) | 386.0 |
| 18 | 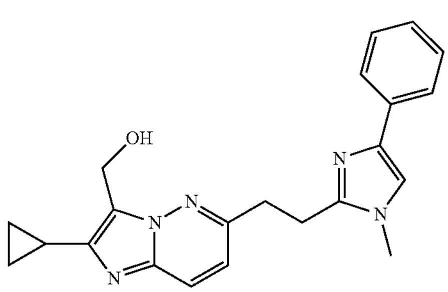 [SMILES: Cn1cc(-c2ccccc2)nc1CCc1ccc2nc(C3CC3)c(CO)n2n1] | (2-Cyclopropyl-6-(2-(1-methyl-4-phenyl-1H-imidazol-2-yl)ethyl)imidazo[1,2-b]pyridazin-3-yl)methanol | (2-Cyclopropyl-6-((1-methyl-4-phenyl-1H-imidazol-2-yl)ethynyl)imidazo[1,2-b]pyridazin-3-yl)methanol (example 6) | 374.0 |

| Expl. No. | Structure | Systematic Name | Starting materials | MW found (MH)+ |
|---|---|---|---|---|
| 19 | 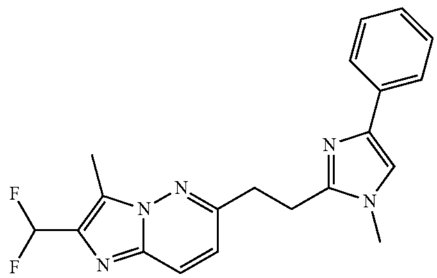 [SMILES: Cc1c(C(F)F)nc2ccc(CCc3nc(-c4ccccc4)cn3C)nn12] | 2-(Difluoromethyl)-3-methyl-6-(2-(1-methyl-4-phenyl-1H-imidazol-2-yl)ethyl)imidazo[1,2-b]pyridazine | 2-(Difluoromethyl)-3-methyl-6-((1-methyl-4-phenyl-1H-imidazol-2-yl)ethynyl)imidazo[1,2-b]pyridazine (example 7) | 368.4 |
| 20 | 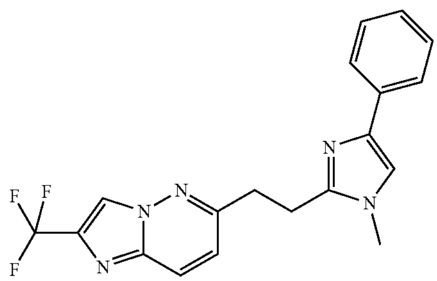 [SMILES: Cn1cc(-c2ccccc2)nc1CCc1ccc2nc(C(F)(F)F)cn2n1] | 6-(2-(1-Methyl-4-phenyl-1H-imidazol-2-yl)ethyl)-2-(trifluoromethyl)imidazo[1,2-b]pyridazine | 6-(1-Methyl-4-phenyl-1H-imidazol-2-ylethynyl)-2-trifluoromethyl-imidazo[1,2-b]pyridazine (example 8) | 372.4 |
| 21 | 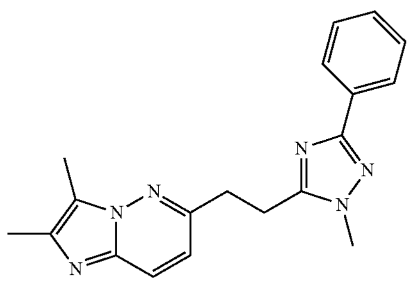 [SMILES: Cc1nc2ccc(CCc3nc(-c4ccccc4)nn3C)nn2c1C] | 2,3-Dimethyl-6-(2-(1-methyl-3-phenyl-1H-1,2,4-triazol-5-yl)ethyl)imidazo[1,2-b]pyridazine | (E)-2,3-Dimethyl-6-(2-(1-methyl-3-phenyl-1H-1,2,4-triazol-5-yl)vinyl)imidazo[1,2-b]pyridazine (example 11) | |
| 22 | 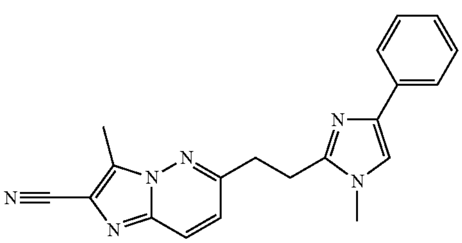 [SMILES: Cc1c(C#N)nc2ccc(CCc3nc(-c4ccccc4)cn3C)nn12] | 3-Methyl-6-[2-(1-methyl-4-phenyl-1H-imidazol-2-yl)-ethyl]-imidazo[1,2-b]pyridazine-2-carbonitrile | (E)-3-Methyl-6-(2-(1-methyl-4-phenyl-1H-imidazol-2-yl)vinyl)imidazo[1,2-b]pyridazine-2-carbonitrile (example 12) | |

Example 23

2,3-Dimethyl-6-(2-(1-methyl-4-(pyrimidin-2-yl)-1H-imidazol-2-yl)ethyl)imidazo[1,2-b]pyridazine

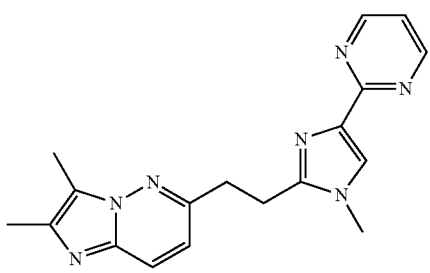 [SMILES: Cc1nc2ccc(CCc3nc(-c4ncccn4)cn3C)nn2c1C]

Step 1: (E)-6-(2-(4-bromo-1-methyl-1H-imidazol-2-yl)vinyl)-2,3-dimethylimidazo[1,2-b]pyridazine To a stirred mixture of 4-bromo-1-methyl-1H-imidazole-2-carbaldehyde (CAS 1262197-89-6; 0.592 g, 3.13 mmol) and ((2,3-dimethylimidazo[1,2-b]pyridazin-6-yl)methyl)triphenylphosphonium chloride (example B.12; 1.43 g, 3.13 mmol) in THF (35 ml) was added at r.t. under an argon atmosphere DBU (1.19 g, 1.18 ml, 7.83 mmol). The mixture was stirred at r.t for 5 hrs. The solid was filtered and washed with THF. The filtrate was evaporated. The crude product was purified by silica gel chromatography using a $CH_2Cl_2$/MeOH gradient as eluent to obtain the title compound (715 mg, 69%) as yellow solid. MS(m/e): 334.4 (M+H)+

Step 2: (E)-2,3-dimethyl-6-(2-(1-methyl-4-(pyrimidin-2-yl)-1H-imidazol-2-yl)vinyl)imidazo[1,2-b]pyridazine To a stirred solution of (E)-6-(2-(4-bromo-1-methyl-1H-imidazol-2-yl)vinyl)-2,3-dimethyl-imidazo[1,2-b]pyridazine (0.4 g, 1.2 mmol) and 2-(tributylstannyl)pyrimidine (444 mg, 1.2 mmol) in DMF (8 ml) under an argon atmosphere was added tetrakis(triphenylphosphine)palladium (0) (70 mg, 60.2 µmol). The mixture was evacuated and back-filled with argon before it was heated to 120° C. overnight, then cooled to r.t. and concentrated. The crude product was purified by silica gel chromatography using a CH$_2$Cl$_2$/MeOH gradient as eluent to obtain the title compound (236 mg, 59%) as yellow solid. MS(m/e): 332.5 (M+H)$^+$

Step 3: 2,3-Dimethyl-6-(2-(1-methyl-4-(pyrimidin-2-yl)-1H-imidazol-2-yl)ethyl)imidazo[1,2-b]pyridazine To a solution of (E)-2,3-dimethyl-6-(2-(1-methyl-4-(pyrimidin-2-yl)-1H-imidazol-2-yl)vinyl)-imidazo[1,2-b]pyridazine (85 mg, 257 mol) in methanol (8 ml) was added Pd/C 10% (small spatula), and the reaction mixture was hydrogenated at normal pressure at r.t overnight. The catalyst was filtered and washed with MeOH. The solvent was evaporated. The crude product was purified by silica gel chromatography using a CH$_2$Cl$_2$/MeOH gradient as eluent to give the title compound (21 mg, 25%) as yellow solid. MS(m/e): 334.5 (M+H)$^+$ In analogy to Example 23, compounds 24 to 29 of the following table were prepared using different tributystannyl heteroaromatic compounds as reactants in the Stille coupling.

| Expl. No. | Structure | Systematic Name | Stille coupling reactant | MW found (M + H)$^+$ |
|---|---|---|---|---|
| 24 | 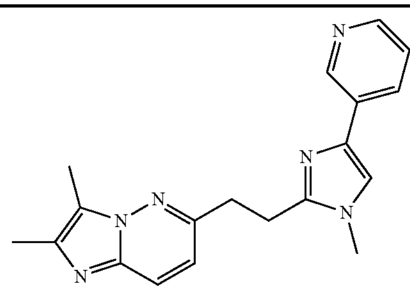 | 2,3-Dimethyl-6-(2-(1-methyl-4-(pyridin-3-yl)-1H-imidazol-2-yl)ethyl)imidazo[1,2-b]pyridazine | 3-(Tributylstannyl)pyridine | 333.5 |
| 25 | 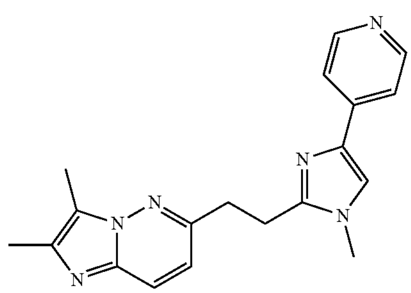 [SMILES: Cc1nc2ccc(CCc3nc(-c4ccncc4)cn3C)nn2c1C] | 2,3-Dimethyl-6-(2-(1-methyl-4-(pyridin-4-yl)-1H-imidazol-2-yl)ethyl)imidazo[1,2-b]pyridazine | 4-(Tributylstannyl)pyridine | 332.4 |
| 26 | 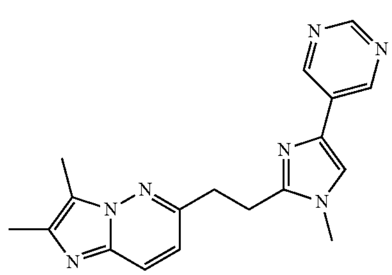 [SMILES: Cc1nc2ccc(CCc3nc(-c4cncnc4)cn3C)nn2c1C] | 2,3-Dimethyl-6-(2-(1-methyl-4-(pyrimidin-5-yl)-1H-imidazol-2-yl)ethyl)imidazo[1,2-b]pyridazine | 5-(Tributylstannyl)pyrimidine | 334.4 |
| 27 | 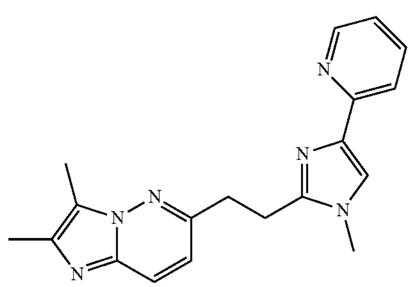 [SMILES: Cc1nc2ccc(CCc3nc(-c4ccccn4)cn3C)nn2c1C] | 2,3-Dimethyl-6-(2-(1-methyl-4-(pyridin-2-yl)-1H-imidazol-2-yl)ethyl)imidazo[1,2-b]pyridazine | 2-(Tributylstannyl)pyridine | 332.4 |

| Expl. No. | Structure | Systematic Name | Stille coupling reactant | MW found (M + H)+ |
|---|---|---|---|---|
| 28 | 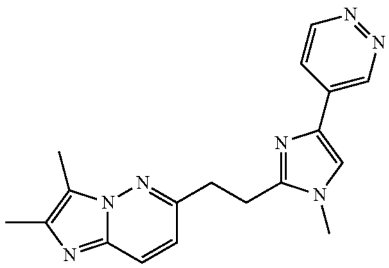 [SMILES: Cc1nc2ccc(CCc3nc(-c4ccnnc4)cn3C)nn2c1C] | 2,3-Dimethyl-6-(2-(1-methyl-4-(pyridazin-4-yl)-1H-imidazol-2-yl)ethyl)imidazo[1,2-b]pyridazine | 4-(Tributylstannyl) pyridazine | 333.4 |
| 29 | 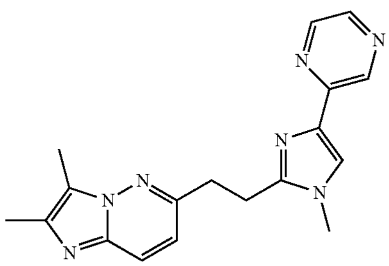 [SMILES: Cc1nc2ccc(CCc3nc(-c4cnccn4)cn3C)nn2c1C] | 2,3-Dimethyl-6-(2-(1-methyl-4-(pyrazin-2-yl)-1H-imidazol-2-yl)ethyl)imidazo[1,2-b]pyridazine | 2-(Tributylstannyl) pyrazine | 333.4 |

Example 30

3,8-Dimethyl-6-(2-(1-methyl-4-(pyridin-2-yl)-1H-imidazol-2-yl)ethyl)-2-(trifluoromethyl)imidazo[1,2-b]pyridazine

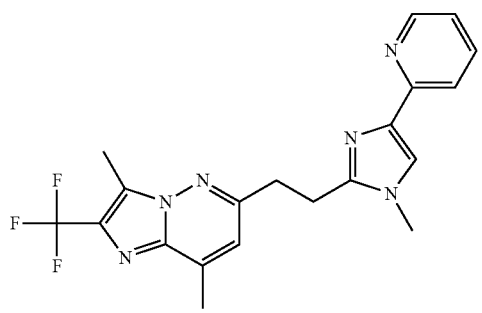 [SMILES: Cc1cc(CCc2nc(-c3ccccn3)cn2C)nn2c(C)c(C(F)(F)F)nc12]

Step 1: (E)-6-(2-(4-Bromo-1-methyl-1H-imidazol-2-yl)vinyl)-3,8-dimethyl-2-(trifluoromethyl)-imidazo[1,2-b]pyridazine To a stirred mixture of 3,8-dimethyl-2-(trifluoromethyl)imidazo[1,2-b]pyridazine-6-carbaldehyde (example B.10; 179 mg, 736 μmol) and ((4-bromo-1-methyl-1H-imidazol-2-yl)methyl)-triphenylphosphonium chloride hydrochloride (example A.4; 561 mg, 1.1 mmol) in THF (6 ml) was added at r.t. and under an argon atmosphere DBU (280 mg, 277 μl, 1.84 mmol). The mixture was stirred at r.t overnight. The solid was filtered and washed with THF. The filtrate was evaporated. The crude product was purified by silica gel chromatography using a CH$_2$Cl$_2$/MeOH gradient as eluent to obtain the title compound (295 mg, 70%) as yellow solid. MS(m/e): 402.3 (M+H)+

Step 2: (E)-3,8-Dimethyl-6-(2-(1-methyl-4-(pyridin-2-yl)-1H-imidazol-2-yl)vinyl)-2-(trifluoro-methyl)imidazo[1,2-b]pyridazine To a stirred solution of (E)-6-(2-(4-bromo-1-methyl-1H-imidazol-2-yl)vinyl)-3,8-dimethyl-2-(trifluoromethyl)imidazo[1,2-b]pyridazine (0.25 g, 500 μmol) and 2-(tributylstannyl)pyridine (221 mg, 600 μmol) in DMF (8 ml) under an argon atmosphere was added tetrakis(triphenylphosphine)palladium (0) (28.9 mg, 25.0 μmol). The mixture was evacuated and back-filled with argon before it was heated to 120° C. overnight, then concentrated. The crude product was purified by silica gel chromatography using a CH$_2$Cl$_2$/MeOH gradient as eluent to obtain the title compound (63 mg, 25%) as off-white solid. MS(m/e): 399.4 (M+H)+

Step 3: 3,8-Dimethyl-6-(2-(1-methyl-4-(pyridin-2-yl)-1H-imidazol-2-yl)ethyl)-2-(trifluoro-methyl)imidazo[1,2-b]pyridazine A solution of (E)-3,8-dimethyl-6-(2-(1-methyl-4-(pyridin-2-yl)-1H-imidazol-2-yl)vinyl)-2-(trifluoromethyl)imidazo[1,2-b]pyridazine (63 mg, 127 μmol) in ethanol (5 ml) was treated with Pd/C 10% (13.5 mg, 12.7 μmol) and hydrogenated at r.t for 8 hrs. The catalyst was filtered and washed with EtOH. The solvent was evaporated. The crude product was purified by silica gel chromatography using a CH$_2$Cl$_2$/MeOH gradient as eluent to obtain the title compound (31 mg, 22%) as off-white solid. MS(m/e): 401.5 (M+H)+

Compound 31 was prepared in analogy to example 30.

| Expl. No. | Structure | Systematic Name | Starting materials | MW found (M + H)+ |
|---|---|---|---|---|
| 31 | 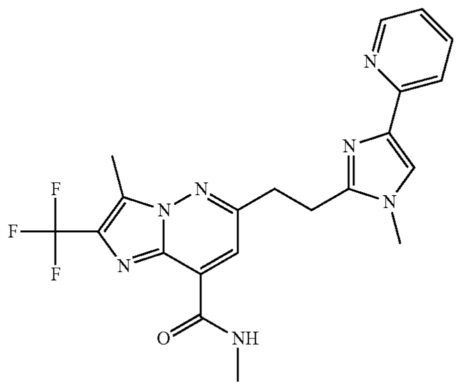 [SMILES: CNC(=O)c1cc(CCc2nc(-c3ccccn3)cn2C)nn2c(C)c(C(F)(F)F)nc12] | N,3-Dimethyl-6-(2-(1-methyl-4-(pyridin-2-yl)-1H-imidazol-2-yl)ethyl)-2-(trifluoromethyl)imidazo[1,2-b]pyridazine-8-carboxamide | 6-Formyl-N,3-dimethyl-2-(trifluoromethyl)imidazo[1,2-b]pyridazine-8-carboxamide (example 11) | 444.4 |

Example 32

2,3-Dimethyl-6-((1-methyl-4-phenyl-1H-imidazol-2-yl)methoxy)imidazo[1,2-b]pyridazine

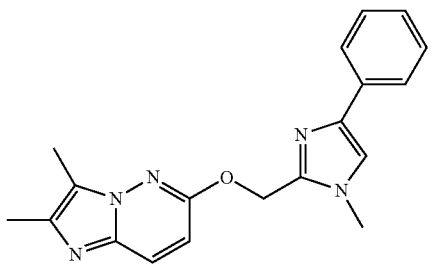 [SMILES: Cc1nc2ccc(OCc3nc(-c4ccccc4)cn3C)nn2c1C]

To a stirred suspension of NaH 55% dispersion in mineral oil (12.0 mg, 275 μmol) at r.t. in DMF (3 ml) under an argon atmosphere was added (1-methyl-4-phenyl-imidazol-2-yl)methanol (CAS 1506492-37-0; 51.8 mg, 275 mol) in one portion. After stirring for 15 min at r.t., 6-chloro-2,3-dimethyl-imidazo[1,2-b]pyridazine (CAS 17412-26-9; 50 mg, 275 mol) was added in one portion and the mixture was stirred at r.t. for overnight. The mixture was diluted with EtOAc and washed with H$_2$O. The aqueous phase was back extracted with EtOAc. The combined organics were washed with H$_2$O and brine, dried over MgSO4, filtered and concentrated to leave a light brown sticky solid. This was triturated in Et20 (10 ml). The suspension was stirred at r.t. for 30 min. The product was collected by filtration, washed with Et20 and dried to provide the title compound (54 mg, 59%) as off-white solid. MS(m/e): 334.1 (M+H)+

In analogy to Example 32, compounds 33 to 46 of the following table were prepared using the appropriate starting materials in the ether formation reaction.

| Expl. No. | Structure | Systematic Name | Starting materials | MW found (M + H)+ |
|---|---|---|---|---|
| 33 | 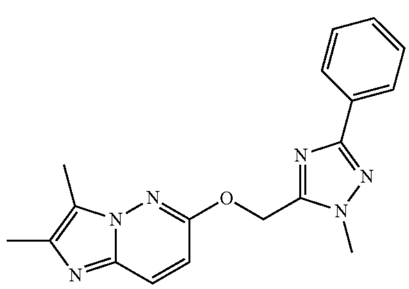 [SMILES: Cc1nc2ccc(OCc3nc(-c4ccccc4)nn3C)nn2c1C] | 2,3-Dimethyl-6-((1-methyl-3-phenyl-1H-1,2,4-triazol-5-yl)methoxy)imidazo[1,2-b]pyridazine | (2-Methyl-5-phenyl-1,2,4-triazol-3-yl)methanol (CAS 881845-15-4) and 6-chloro-2,3-dimethyl-imidazo[1,2-b]pyridazine (CAS 17412-26-9) | 335.3 |

-continued

| Expl. No. | Structure | Systematic Name | Starting materials | MW found (M + H)+ |
|---|---|---|---|---|
| 34 | 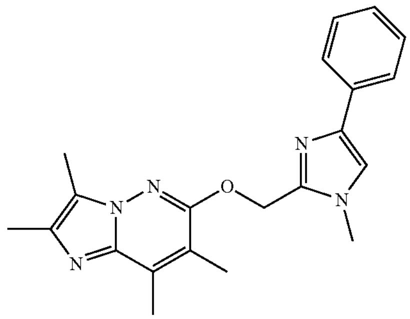 [SMILES: Cc1nc2c(C)c(C)c(OCc3nc(-c4ccccc4)cn3C)nn2c1C] | 2,3,7,8-Tetramethyl-6-((1-methyl-4-phenyl-1H-imidazol-2-yl)methoxy)imidazo[1,2-b]pyridazine | (1-Methyl-4-phenyl-imidazol-2-yl)methanol (CAS 1506492-37-0) and 6-chloro-2,3,7,8-tetramethyl-imidazo[1,2-b]pyridazine (CAS 17412-25-8) | 361.4 |
| 35 | 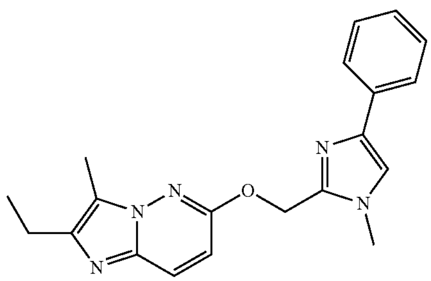 [SMILES: CCc1nc2ccc(OCc3nc(-c4ccccc4)cn3C)nn2c1C] | 2-Ethyl-3-methyl-6-((1-methyl-4-phenyl-1H-imidazol-2-yl)methoxy)imidazo[1,2-b]pyridazine | (1-Methyl-4-phenyl-imidazol-2-yl)methanol (CAS 1506492-37-0) and 6-chloro-2-ethyl-3-methyl-imidazo[1,2-b]pyridazine | 347.4 |
| 36 | 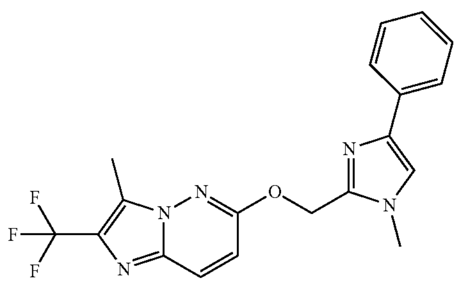 | 3-Methyl-6-((1-methyl-4-phenyl-1H-imidazol-2-yl)methoxy)-2-(trifluoromethyl)imidazo[1,2-b]pyridazine | (1-Methyl-4-phenyl-imidazol-2-yl)methanol (CAS 1506492-37-0) and 6-chloro-3-methyl-2-(trifluoromethyl)imidazo[1,2-b]pyridazine (CAS 916256-80-9) | 387.4 |
| 37 | 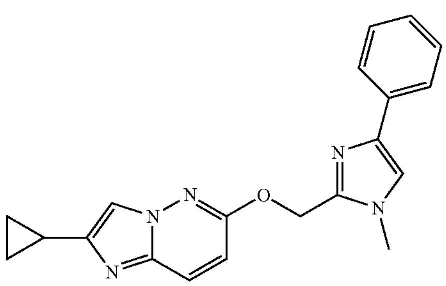 [SMILES: Cn1cc(-c2ccccc2)nc1COc1ccc2nc(C3CC3)cn2n1] | 2-Cyclopropyl-6-((1-methyl-4-phenyl-1H-imidazol-2-yl)methoxy)imidazo[1,2-b]pyridazine | (1-Methyl-4-phenyl-imidazol-2-yl)methanol (CAS 1506492-37-0) and 6-chloro-2-cyclopropyl-imidazo[1,2-b]pyridazine (CAS 916257-51-7) | 345.4 |
| 38 | 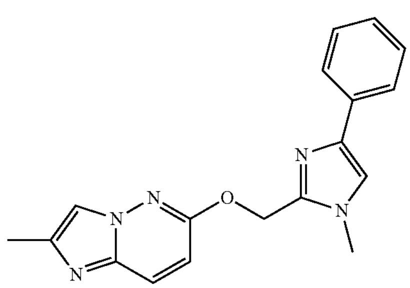 [SMILES: Cc1cn2nc(OCc3nc(-c4ccccc4)cn3C)ccc2n1] | 2-Methyl-6-((1-methyl-4-phenyl-1H-imidazol-2-yl)methoxy)imidazo[1,2-b]pyridazine | (1-Methyl-4-phenyl-imidazol-2-yl)methanol (CAS 1506492-37-0) and 6-chloro-2-methyl-imidazo[1,2-b]pyridazine (CAS 14793-00-1) | 319.4 |

-continued

| Expl. No. | Structure | Systematic Name | Starting materials | MW found (M + H)+ |
|---|---|---|---|---|
| 39 | 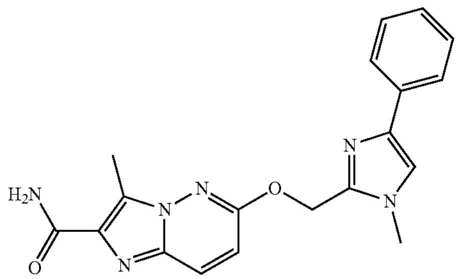 [SMILES: Cc1c(C(N)=O)nc2ccc(OCc3nc(-c4ccccc4)cn3C)nn12] | 3-Methyl-6-((1-methyl-4-phenyl-1H-imidazol-2-yl)methoxy)imidazo[1,2-b]pyridazine-2-carboxamide | (1-Methyl-4-phenyl-imidazol-2-yl)methanol (CAS 1506492-37-0) and 6-chloro-3-methyl-imidazo[1,2-b]pyridazine-2-carboxamide (CAS 1500104-11-9) | 362.4 |
| 40 | 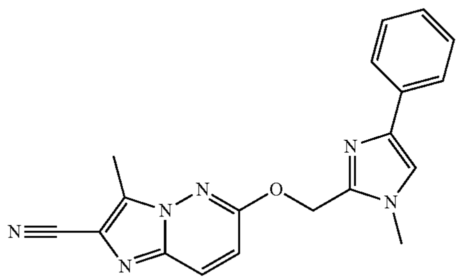 [SMILES: Cc1c(C#N)nc2ccc(OCc3nc(-c4ccccc4)cn3C)nn12] | 3-Methyl-6-((1-methyl-4-phenyl-1H-imidazol-2-yl)methoxy)imidazo[1,2-b]pyridazine-2-carbonitrile | (1-Methyl-4-phenyl-imidazol-2-yl)methanol (CAS 1506492-37-0) and 6-chloro-3-methyl-imidazo[1,2-b]pyridazine-2-carbonitrile (CAS 1610007-73-2) | 344.4 |
| 41 | 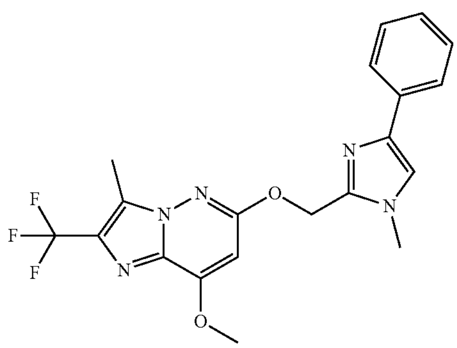 [SMILES: COc1cc(OCc2nc(-c3ccccc3)cn2C)nn2c(C)c(C(F)(F)F)nc12] | 8-Methoxy-3-methyl-6-((1-methyl-4-phenyl-1H-imidazol-2-yl)methoxy)-2-(trifluoromethyl)imidazo[1,2-b]pyridazine | (1-Methyl-4-phenyl-imidazol-2-yl)methanol (CAS 1506492-37-0) and 6-chloro-8-methoxy-3-methyl-2-(trifluoromethyl)imidazo[1,2-b]pyridazine (example B.13) | 417.4 |
| 42 | 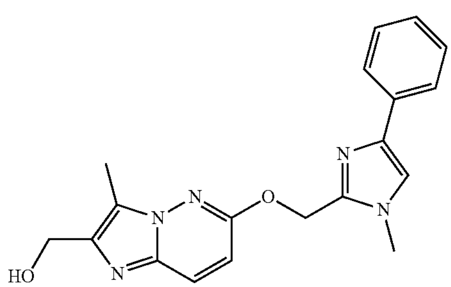 [SMILES: Cc1c(CO)nc2ccc(OCc3nc(-c4ccccc4)cn3C)nn12] | (3-Methyl-6-((1-methyl-4-phenyl-1H-imidazol-2-yl)methoxy)imidazo[1,2-b]pyridazin-2-yl)methanol | (1-Methyl-4-phenyl-imidazol-2-yl)methanol (CAS 1506492-37-0) and (6-chloro-3-methyl-imidazo[1,2-b]pyridazin-2-yl)methanol (CAS 1315359-36-4) | 349.4 |
| 43 | 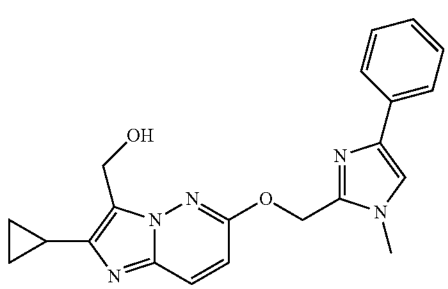 [SMILES: Cn1cc(-c2ccccc2)nc1COc1ccc2nc(C3CC3)c(CO)n2n1] | (2-Cyclopropyl-6-((1-methyl-4-phenyl-1H-imidazol-2-yl)methoxy)imidazo[1,2-b]pyridazin-3-yl)methanol | (1-Methyl-4-phenyl-imidazol-2-yl)methanol (CAS 1506492-37-0) and (6-chloro-2-cyclopropyl-imidazo[1,2-b]pyridazin-3-yl)methanol (CAS 916257-63-1) | 375.4 |

| Expl. No. | Structure | Systematic Name | Starting materials | MW found (M + H)+ |
|---|---|---|---|---|
| 44 | 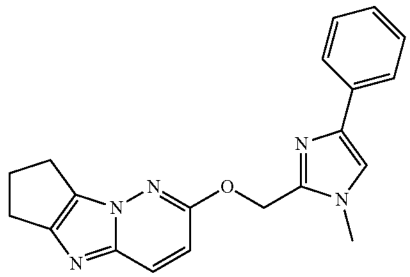 [SMILES: Cn1cc(-c2ccccc2)nc1COc1ccc2nc3c(n2n1)CCC3] | 2-[(1-Methyl-4-phenyl-imidazol-2-yl)methoxy]-7,8-dihydro-6H-cyclopenta[1,2]imidazo[3,4-c]pyridazine | (1-Methyl-4-phenyl-imidazol-2-yl)methanol (CAS 1506492-37-0) and 2-chloro-7,8-dihydro-6H-cyclopenta[1,2]imidazo[3,4-c]pyridazine (CAS 1610008-02-0) | 345.4 |
| 45 | 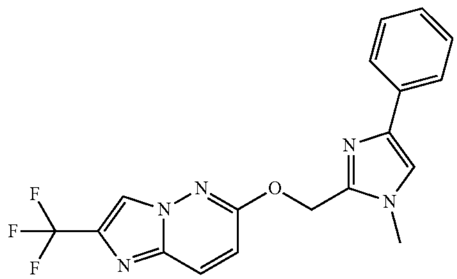 [SMILES: Cn1cc(-c2ccccc2)nc1COc1ccc2nc(C(F)(F)F)cn2n1] | 6-((1-Methyl-4-phenyl-1H-imidazol-2-yl)methoxy)-2-(trifluoromethyl)imidazo[1,2-b]pyridazine | (1-Methyl-4-phenyl-imidazol-2-yl)methanol (CAS 1506492-37-0) and 6-chloro-2-(trifluoromethyl)imidazo[1,2-b]pyridazine (CAS 109113-97-5) | 373.3 |
| 46 | 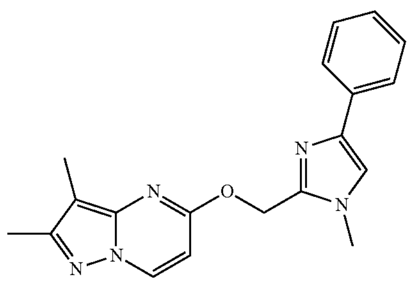 [SMILES: Cc1nn2ccc(OCc3nc(-c4ccccc4)cn3C)nc2c1C] | 2,3-Dimethyl-5-((1-methyl-4-phenyl-1H-imidazol-2-yl)methoxy)pyrazolo[1,5-a]pyrimidine | (1-Methyl-4-phenyl-imidazol-2-yl)methanol (CAS 1506492-37-0) and 5-chloro-2,3-dimethylpyrazolo[1,5-a]pyrimidine (example B.1) | 333.4 |

We claim:

1. A compound of formula I

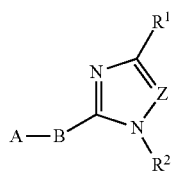

(I)

wherein A is

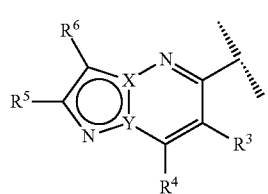

$R^1$ is selected from aryl or heteroaryl,
$R^2$ is selected from hydrogen or $C_{1-7}$ alkyl,
$R^3$ is selected from hydrogen or $C_{1-7}$ alkyl,
$R^4$ is selected from hydrogen, $C_{1-7}$ alkyl, $C_{1-7}$ alkoxy or C(O)NR'R",
$R^5$ is selected from $C_{1-7}$ alkyl, $C_{3-8}$ cycloalkyl, $C_{1-7}$ haloalkyl, cyano, $C_{1-7}$ hydroxyalkyl or C(O)NR'R",
$R^6$ is selected from hydrogen, $C_{1-7}$ alkyl or $C_{1-7}$ hydroxyalkyl, or
$R^5$ and $R^6$ form together $C_{3-8}$ cycloalkyl,
R' and R" are in each occurrence independently selected from hydrogen or $C_{1-7}$ alkyl,
X and Y are independently selected from C or N, with the proviso that X and Y are not simultaneously N,
Z is selected from CH or N,
B is selected from $C_1$-$C_4$ alkylene, $C_2$-$C_4$ alkenylene, $C_2$-$C_4$-alkynylene or —O—$C_1$-$C_4$-alkyl.

2. The compound of claim 1 wherein Z is CH.

3. The compound of claim 1 wherein $R^1$ is a six membered aryl or a six membered heteroaryl group containing at least one N atom.

4. The compound of claim 3, wherein $R^1$ is selected from phenyl, pyridazinyl, pyrimidinyl, pyridinyl, pyrazinyl.

5. The compound of claim 4 wherein $R^1$ is phenyl.

6. The compound of claim 4 wherein Z is CH.

7. The compound of claim 1 wherein B is selected from ethylene, ethenylene, ethynylene or —O—$CH_2$—.

8. The compound according to claim 7 wherein:
B is selected from ethylene, ethenylene, ethynylene or —O—$CH_2$—;

Z is CH; and,
R¹ is selected from phenyl, pyridazinyl, pyrimidinyl, pyridinyl or pyrazinyl.

9. The compound of claim 1 wherein:

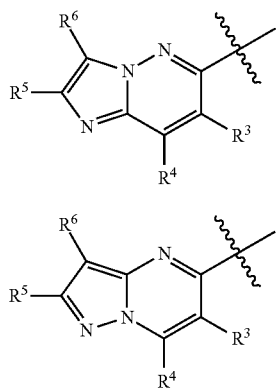

A is (a) or (b),
R³ is hydrogen or methyl,
R⁴ is hydrogen, methyl, methoxy or C(O)NR'R" wherein R' and R" are independently selected from hydrogen and methyl,
R⁵ is methyl, ethyl, cyclopropyl, halomethyl, cyano or —C(O)NH₂,
R⁶ is hydrogen, methyl or hydroxymethyl.

10. The compound of claim 1 said compound selected from the group consisting of:
2,3-dimethyl-6-((1-methyl-4-phenyl-1H-imidazol-2-yl)ethynyl)imidazo[1,2-b]pyridazine;
2,3,7,8-tetramethyl-6-((1-methyl-4-phenyl-1H-imidazol-2-yl)ethynyl)imidazo[1,2-b]pyridazine;
(2-methyl-6-((1-methyl-4-phenyl-1H-imidazol-2-yl)ethynyl)imidazo[1,2-b]pyridazin-3-yl)methanol;
2,3-dimethyl-5-((1-methyl-4-phenyl-1H-imidazol-2-yl)ethynyl)pyrazolo[1,5-a]pyrimidine;
3-methyl-6-((1-methyl-4-phenyl-1H-imidazol-2-yl)ethynyl)-2-(trifluoromethyl)imidazo[1,2-b]pyridazine;
(2-cyclopropyl-6-((1-methyl-4-phenyl-1H-imidazol-2-yl)ethynyl)imidazo[1,2-b]pyridazin-3-yl)methanol;
2-(difluoromethyl)-3-methyl-6-((1-methyl-4-phenyl-1H-imidazol-2-yl)ethynyl)imidazo[1,2-b]pyridazine;
6-(1-Methyl-4-phenyl-1H-imidazol-2-ylethynyl)-2-trifluoromethyl-imidazo[1,2-b]pyridazine;
3-Methyl-6-(1-methyl-4-phenyl-1H-imidazol-2-ylethynyl)-imidazo[1,2-b]pyridazine-2-carbonitrile;
2-cyclopropyl-3-methyl-6-((1-methyl-4-phenyl-1H-imidazol-2-yl)ethynyl)imidazo[1,2-b]pyridazine;
(E)-2,3-dimethyl-6-(2-(1-methyl-3-phenyl-1H-1,2,4-triazol-5-yl)vinyl)imidazo[1,2-b]pyridazine;
(E)-3-methyl-6-(2-(1-methyl-4-phenyl-1H-imidazol-2-yl)vinyl)imidazo[1,2-b]pyridazine-2-carbonitrile;
2,3-dimethyl-6-(2-(1-methyl-4-phenyl-1H-imidazol-2-yl)ethyl)imidazo[1,2-b]pyridazine;
2,3,7,8-tetramethyl-6-(2-(1-methyl-4-phenyl-1H-imidazol-2-yl)ethyl)imidazo[1,2-b]pyridazine;
(2-methyl-6-(2-(1-methyl-4-phenyl-1H-imidazol-2-yl)ethyl)imidazo[1,2-b]pyridazin-3-yl)methanol;
2,3-dimethyl-5-(2-(1-methyl-4-phenyl-1H-imidazol-2-yl)ethyl)pyrazolo[1,5-a]pyrimidine;
3-methyl-6-(2-(1-methyl-4-phenyl-1H-imidazol-2-yl)ethyl)-2-(trifluoromethyl)imidazo[1,2-b]pyridazine;
(2-cyclopropyl-6-(2-(1-methyl-4-phenyl-1H-imidazol-2-yl)ethyl)imidazo[1,2-b]pyridazin-3-yl)methanol;
2-(difluoromethyl)-3-methyl-6-(2-(1-methyl-4-phenyl-1H-imidazol-2-yl)ethyl)imidazo[1,2-b]pyridazine;
6-(2-(1-methyl-4-phenyl-1H-imidazol-2-yl)ethyl)-2-(trifluoromethyl)imidazo[1,2-b]pyridazine;
2,3-dimethyl-6-(2-(1-methyl-3-phenyl-1H-1,2,4-triazol-5-yl)ethyl)imidazo[1,2-b]pyridazine;
3-Methyl-6-[2-(1-methyl-4-phenyl-1H-imidazol-2-yl)-ethyl]-imidazo[1,2-b]pyridazine-2-carbonitrile;
2,3-dimethyl-6-(2-(1-methyl-4-(pyrimidin-2-yl)-1H-imidazol-2-yl)ethyl)imidazo[1,2-b]pyridazine;
2,3-dimethyl-6-(2-(1-methyl-4-(pyridin-3-yl)-1H-imidazol-2-yl)ethyl)imidazo[1,2-b]pyridazine;
2,3-dimethyl-6-(2-(1-methyl-4-(pyridin-4-yl)-1H-imidazol-2-yl)ethyl)imidazo[1,2-b]pyridazine;
2,3-dimethyl-6-(2-(1-methyl-4-(pyrimidin-5-yl)-1H-imidazol-2-yl)ethyl)imidazo[1,2-b]pyridazine;
2,3-dimethyl-6-(2-(1-methyl-4-(pyridin-2-yl)-1H-imidazol-2-yl)ethyl)imidazo[1,2-b]pyridazine;
2,3-dimethyl-6-(2-(1-methyl-4-(pyridazin-4-yl)-1H-imidazol-2-yl)ethyl)imidazo[1,2-b]pyridazine;
2,3-dimethyl-6-(2-(1-methyl-4-(pyrazin-2-yl)-1H-imidazol-2-yl)ethyl)imidazo[1,2-b]pyridazine;
3,8-dimethyl-6-(2-(1-methyl-4-(pyridin-2-yl)-1H-imidazol-2-yl)ethyl)-2-(trifluoromethyl)imidazo[1,2-b]pyridazine;
N,3-dimethyl-6-(2-(1-methyl-4-(pyridin-2-yl)-1H-imidazol-2-yl)ethyl)-2-(trifluoromethyl)imidazo[1,2-b]pyridazine-8-carboxamide;
2,3-dimethyl-6-((1-methyl-3-phenyl-1H-1,2,4-triazol-5-yl)methoxy)imidazo[1,2-b]pyridazine;
2,3,7,8-tetramethyl-6-((1-methyl-4-phenyl-1H-imidazol-2-yl)methoxy)imidazo[1,2-b]pyridazine;
2-ethyl-3-methyl-6-((1-methyl-4-phenyl-1H-imidazol-2-yl)methoxy)imidazo[1,2-b]pyridazine;
2-ethyl-3-methyl-6-((1-methyl-4-phenyl-1H-imidazol-2-yl)methoxy)imidazo[1,2-b]pyridazine;
3-methyl-6-((1-methyl-4-phenyl-1H-imidazol-2-yl)methoxy)-2-(trifluoromethyl)imidazo[1,2-b]pyridazine;
2-cyclopropyl-6-((1-methyl-4-phenyl-1H-imidazol-2-yl)methoxy)imidazo[1,2-b]pyridazine;
2-methyl-6-((1-methyl-4-phenyl-1H-imidazol-2-yl)methoxy)imidazo[1,2-b]pyridazine;
3-methyl-6-((1-methyl-4-phenyl-1H-imidazol-2-yl)methoxy)imidazo[1,2-b]pyridazine-2-carboxamide;
3-methyl-6-((1-methyl-4-phenyl-1H-imidazol-2-yl)methoxy)imidazo[1,2-b]pyridazine-2-carbonitrile;
8-methoxy-3-methyl-6-((1-methyl-4-phenyl-1H-imidazol-2-yl)methoxy)-2-(trifluoromethyl)imidazo[1,2-b]pyridazine;
(3-methyl-6-((1-methyl-4-phenyl-1H-imidazol-2-yl)methoxy)imidazo[1,2-b]pyridazin-2-yl)methanol;
(2-cyclopropyl-6-((1-methyl-4-phenyl-1H-imidazol-2-yl)methoxy)imidazo[1,2-b]pyridazin-3-yl)methanol;
6-((1-methyl-4-phenyl-1H-imidazol-2-yl)methoxy)-2-(trifluoromethyl)imidazo[1,2-b]pyridazine;
2,3-dimethyl-5-((1-methyl-4-phenyl-1H-imidazol-2-yl)methoxy)pyrazolo[1,5-a]pyrimidine; and, 2-[(1-Methyl-4-phenyl-imidazol-2-yl)methoxy]-7,8-dihydro-6H-cyclopenta[1,2]imidazo[3,4-c]pyridazine;
or,
a pharmaceutically acceptable salt thereof.

11. A pharmaceutical composition comprising a compound of claim 1 and at least 1 carrier, diluent or excipient.

* * * * *